US009931425B2

(12) United States Patent
Edwards et al.

(10) Patent No.: US 9,931,425 B2
(45) Date of Patent: Apr. 3, 2018

(54) SYSTEMS, METHODS AND ARTICLES TO PROVIDE OLFACTORY SENSATIONS

(71) Applicants: David A. Edwards, Boston, MA (US); Rachel Diane Field, Huntington Beach, CA (US); Amy Michelle Yin, Onalaska, WI (US); Eyal Shahar, Paris (FR)

(72) Inventors: David A. Edwards, Boston, MA (US); Rachel Diane Field, Huntington Beach, CA (US); Amy Michelle Yin, Onalaska, WI (US); Eyal Shahar, Paris (FR)

(73) Assignees: VAPOR COMMUNICATIONS, INC., Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 67 days.

(21) Appl. No.: 14/213,608

(22) Filed: Mar. 14, 2014

(65) Prior Publication Data
US 2015/0048178 A1    Feb. 19, 2015

Related U.S. Application Data

(60) Provisional application No. 61/792,716, filed on Mar. 15, 2013, provisional application No. 61/817,180, filed on Apr. 29, 2013.

(51) Int. Cl.
*A61L 9/00* (2006.01)
*A61L 9/03* (2006.01)
(Continued)

(52) U.S. Cl.
CPC .............. *A61L 9/032* (2013.01); *A61L 9/035* (2013.01); *A61L 9/122* (2013.01); *A63J 5/00* (2013.01);
(Continued)

(58) Field of Classification Search
CPC . A61L 9/03; A61L 9/032; A61L 9/035; A61L 9/02
(Continued)

(56) References Cited

U.S. PATENT DOCUMENTS

| D163,210 S | 5/1951 | Long |
| D247,533 S | 3/1978 | Noyes |

(Continued)

FOREIGN PATENT DOCUMENTS

| CN | 1642583 A | 7/2005 |
| CN | 100461154 C | 2/2009 |

(Continued)

OTHER PUBLICATIONS

Boehret, "Does your air freshener need an app?" *The Verge*, Apr. 27, 2016, retrieved from URL=http//www.theverge.com/2016/4/27/11514206/your-air-freshener-just-got-a-lot-smarter, downloaded May 18, 2016, 5 pages.

(Continued)

*Primary Examiner* — Viet Le
(74) *Attorney, Agent, or Firm* — Seed IP Law Group LLP

(57) ABSTRACT

A system to provide scents includes a scent receiver to replaceable receive scent carriers that carry scent media, a scent actuator operable to controllable release scent, and a configurable circulation subsystem. Peltier devices may used to induce active heating and active cooling of scent media according to defined scent sequence information or scent tracks. The system is also operable to collect air, including scents, from an ambient environment, and temporarily retaining such for sampling by a user. Scent tracks may be defined and shared amongst users and other entities.

22 Claims, 17 Drawing Sheets

(51) Int. Cl.

| | | |
|---|---|---|
| *G06F 3/01* | (2006.01) | |
| *A61L 9/12* | (2006.01) | |
| *H04M 1/05* | (2006.01) | |
| *H04M 1/21* | (2006.01) | |
| *H04N 21/41* | (2011.01) | |
| *A63J 5/00* | (2006.01) | |
| *H04N 21/414* | (2011.01) | |
| *H04N 21/436* | (2011.01) | |

(52) U.S. Cl.
CPC .......... *G06F 3/011* (2013.01); *A61L 2209/11* (2013.01); *A61L 2209/133* (2013.01); *A61L 2209/134* (2013.01); *A61L 2209/14* (2013.01); *A63J 2005/008* (2013.01); *H04M 1/05* (2013.01); *H04M 1/21* (2013.01); *H04M 2250/12* (2013.01); *H04N 21/4104* (2013.01); *H04N 21/41415* (2013.01); *H04N 21/43615* (2013.01)

(58) Field of Classification Search
USPC .................................................. 239/690, 261
See application file for complete search history.

(56) References Cited

U.S. PATENT DOCUMENTS

| | | | |
|---|---|---|---|
| 4,258,874 A | 3/1981 | Webinger et al. | |
| D281,281 S | 11/1985 | Matalon | |
| 4,583,686 A | 4/1986 | Martens et al. | |
| D288,713 S | 3/1987 | Darneal | |
| D306,235 S | 2/1990 | Tamamura | |
| 4,968,456 A | 11/1990 | Muderlak et al. | |
| D315,789 S | 3/1991 | Muderlak | |
| D321,284 S | 11/1991 | Marsella et al. | |
| D327,037 S | 6/1992 | Martineau | |
| 5,195,633 A | 3/1993 | Kaminski | |
| 5,273,690 A | 12/1993 | McDowell | |
| D349,335 S | 8/1994 | Wang | |
| D363,509 S | 10/1995 | Parekh et al. | |
| D381,515 S | 7/1997 | Haynes | |
| D411,881 S | 7/1999 | Weick | |
| D431,902 S | 10/2000 | Mellin | |
| D438,608 S | 3/2001 | Chen | |
| D446,849 S | 8/2001 | Weinberg | |
| 6,581,915 B2 | 6/2003 | Bartsch et al. | |
| D477,390 S | 7/2003 | Chen | |
| 6,654,664 B1 | 11/2003 | Chiao | |
| D496,451 S | 9/2004 | Julos et al. | |
| D496,585 S | 9/2004 | McBride et al. | |
| 6,803,987 B2 * | 10/2004 | Manne .................. | A61L 9/122 352/85 |
| D512,494 S | 12/2005 | Haranaka | |
| D513,070 S | 12/2005 | Haranaka | |
| D519,624 S | 4/2006 | Chen | |
| D525,488 S | 7/2006 | McWhorter | |
| D525,871 S | 8/2006 | Zeh et al. | |
| D527,182 S | 8/2006 | Ham | |
| D532,695 S | 11/2006 | Grant | |
| D548,317 S | 8/2007 | Newton et al. | |
| D548,969 S | 8/2007 | Bramley | |
| D560,788 S | 1/2008 | Farrell et al. | |
| D574,072 S | 7/2008 | Carlson et al. | |
| 7,400,822 B2 | 7/2008 | Ruiz Ballesteros et al. | |
| D575,384 S | 8/2008 | Huang | |
| D575,859 S | 8/2008 | Scimone | |
| D575,860 S | 8/2008 | Wu | |
| D582,534 S | 12/2008 | Conway et al. | |
| D583,450 S | 12/2008 | Choi | |
| D583,451 S | 12/2008 | Aloe et al. | |
| D583,452 S | 12/2008 | Aloe et al. | |
| D593,669 S | 6/2009 | Daelemans et al. | |
| D597,192 S | 7/2009 | Drucker et al. | |
| D601,343 S | 10/2009 | Franczyk et al. | |
| D604,099 S | 11/2009 | Mishan | |
| D611,584 S | 3/2010 | Gruenbacher et al. | |
| D611,585 S | 3/2010 | Gruenbacher et al. | |
| D625,398 S | 10/2010 | Choi | |
| 7,824,627 B2 | 11/2010 | Michaels et al. | |
| D633,610 S | 3/2011 | Wu | |
| D634,538 S | 3/2011 | Dumas | |
| D637,274 S | 5/2011 | Chan et al. | |
| D643,103 S | 8/2011 | Bilko et al. | |
| D644,725 S | 9/2011 | Kim | |
| D647,187 S | 10/2011 | Chan et al. | |
| D647,193 S | 10/2011 | Kim | |
| 8,032,014 B2 | 10/2011 | Cheung | |
| D654,761 S | 2/2012 | Herbst | |
| D656,230 S | 3/2012 | Robinson et al. | |
| D662,578 S | 6/2012 | Blanking et al. | |
| D662,579 S | 6/2012 | Blanking et al. | |
| D662,580 S | 6/2012 | Blanking et al. | |
| D672,860 S | 12/2012 | Blachford et al. | |
| D675,304 S | 1/2013 | Valentino et al. | |
| D675,434 S | 2/2013 | Vernall et al. | |
| D676,239 S | 2/2013 | Benoit et al. | |
| D680,637 S | 4/2013 | Blachford et al. | |
| D681,182 S | 4/2013 | Tómas Vilarara et al. | |
| D681,183 S | 4/2013 | Blachford et al. | |
| D686,817 S | 7/2013 | Dennis | |
| D689,999 S | 9/2013 | Viala | |
| D705,918 S | 5/2014 | Robinson et al. | |
| D715,051 S | 10/2014 | Tung et al. | |
| D716,432 S | 10/2014 | Viala et al. | |
| D716,433 S | 10/2014 | Milon et al. | |
| D720,526 S | 1/2015 | Lopez-Stout | |
| D729,369 S | 5/2015 | Viala et al. | |
| 2002/0066798 A1 | 6/2002 | Laudamiel-Pellet et al. | |
| 2002/0068009 A1 | 6/2002 | Laudamiel-Pellet et al. | |
| 2003/0020185 A1 | 1/2003 | Cox | |
| 2003/0175148 A1 | 9/2003 | Kvietok et al. | |
| 2003/0206834 A1 | 11/2003 | Chiao et al. | |
| 2005/0160789 A1 | 7/2005 | Freyer et al. | |
| 2005/0163649 A1 * | 7/2005 | Friedrich .................. | A61L 9/02 422/1 |
| 2005/0195367 A1 | 9/2005 | Selander et al. | |
| 2005/0265904 A1 | 12/2005 | Hardy et al. | |
| 2005/0278224 A1 * | 12/2005 | Bannai .................... | A61L 9/035 705/22 |
| 2006/0037970 A1 * | 2/2006 | Fazzio .................... | A45D 34/02 222/145.1 |
| 2006/0039835 A1 | 2/2006 | Nottingham et al. | |
| 2006/0155225 A1 | 7/2006 | Murdock et al. | |
| 2007/0041865 A1 | 2/2007 | Ayoub et al. | |
| 2007/0258849 A1 | 11/2007 | Kent | |
| 2007/0262477 A1 * | 11/2007 | Brown .................... | A61L 9/035 261/19 |
| 2008/0292508 A1 | 11/2008 | Zlotnik et al. | |
| 2010/0096409 A1 | 4/2010 | Wainwright | |
| 2010/0114819 A1 | 5/2010 | Kim et al. | |
| 2010/0243754 A1 | 9/2010 | Harris | |
| 2010/0309434 A1 * | 12/2010 | Van Schijndel ........ | A61L 9/125 352/85 |
| 2011/0226864 A1 | 9/2011 | Kim et al. | |
| 2011/0247718 A1 | 10/2011 | Samain | |
| 2013/0173315 A1 | 7/2013 | Dorsey | |
| 2013/0304255 A1 | 11/2013 | Ratnakar | |
| 2014/0377130 A1 | 12/2014 | Edwards et al. | |

FOREIGN PATENT DOCUMENTS

| | | |
|---|---|---|
| DE | 100 65 5545 A1 | 7/2002 |
| DE | 100 65 545 A1 | 11/2009 |
| EP | 1 098 195 A2 | 5/2001 |
| JP | 2009-265453 A | 11/2009 |
| JP | 2012-198694 A | 10/2012 |
| WO | 02/09772 A2 | 2/2002 |
| WO | 02/09773 A2 | 2/2002 |
| WO | 02/09776 A2 | 2/2002 |
| WO | 03/077962 A2 | 9/2003 |
| WO | 2012/038477 A1 | 3/2012 |
| WO | 2015/195548 A1 | 12/2012 |
| WO | 2014/144636 A2 | 9/2014 |

(56) References Cited

FOREIGN PATENT DOCUMENTS

| WO | 2014/144690 A2 | 9/2014 |
| WO | 2015/057798 A1 | 4/2015 |
| WO | 2015/130347 A1 | 9/2015 |
| WO | 2015/130348 A1 | 9/2015 |

OTHER PUBLICATIONS

Edwards et al., "Systems, Methods and Articles to Provide Olfactory Sensations," Preliminary Amendment, filed Sep. 4, 2014, for U.S. Appl. No. 14/213,683, 7 pages.
Edwards et al., "Systems, Methods and Articles to Provide Olfactory Sensations," Restriction Requirement, dated Feb. 25, 2016, for U.S. Appl. No. 14/213,683, 8 pages.
Edwards et al., "Systems, Methods and Articles to Provide Olfactory Sensations," Response to Restriction Requirement, filed Apr. 25, 2016, for U.S. Appl. No. 14/213,683, 10 pages.
International Search Report dated Dec. 17, 2014, for International Application No. PCT/US2014/029132, 5 pages.
International Search Report dated Feb. 9, 2015, for International Application No. PCT/US2014/029208, 5 pages.
International Search Report dated Jan. 16, 2015, for International Application No. PCT/US2014/060630, 3 pages.
International Search Report dated Jan. 12, 2015, for International Application No. PCT/US2014/060614, 3 pages.
International Search Report dated Feb. 3, 2015, for International Application No. PCT/US2014/060643, 3 pages.
International Search Report dated Sep. 21, 2015, for International Application No. PCT/US2015/035805, 3 pages.
Written Opinion dated Dec. 17, 2014, for International Application No. PCT/US2014/029132, 11 pages.
Written Opinion dated Feb. 9, 2015, for International Application No. PCT/US2014/029208, 11 pages.
Written Opinion dated Jan. 16, 2015, for International Application No. PCT/US2014/060630, 17 pages.
Written Opinion dated Jan. 12, 2015, for International Application No. PCT/US2014/060614, 10 pages.
Written Opinion dated Feb. 3, 2015, for International Application No. PCT/US2014/060643, 7 pages.
Written Opinion dated Sep. 21, 2015, for International Application No. PCT/US2015/035805, 8 pages.
International Preliminary Report on Patentability with Written Opinion dated Sep. 15, 2015 for International Application No. PCT/US2014/029208, 11 pages.
International Preliminary Report on Patentability with Written Opinion dated Sep. 15, 2015 for International Application No. PCT/US2014/029132, 12 pages.
Chinese Office Action, dated Apr. 19, 2017, for Chinese Application No. 201480025108.4, 8 pages.
Chinese Office Action, dated Mar. 2, 2017, for Chinese Application No. 201480022939.6, 4 pages.

\* cited by examiner

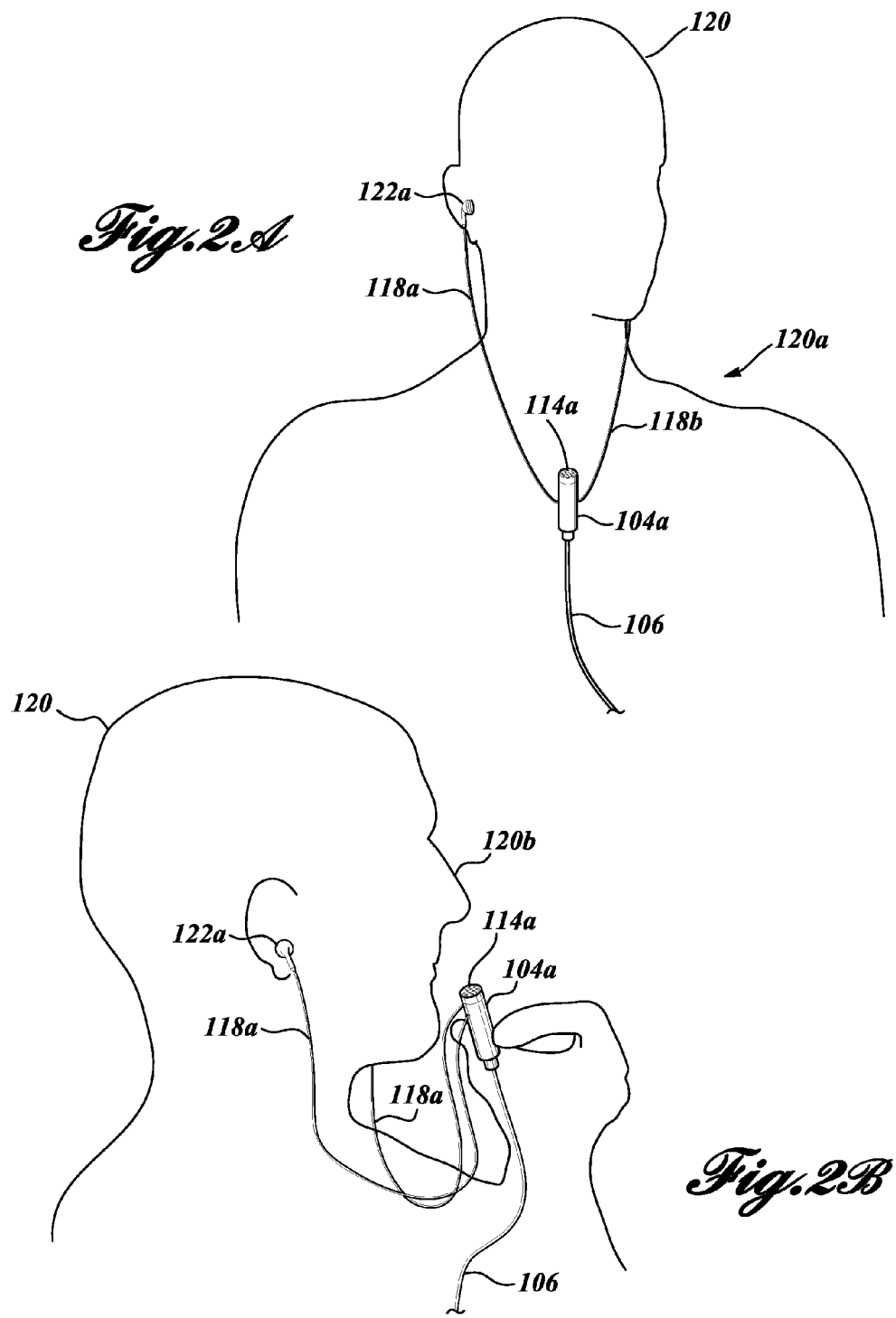

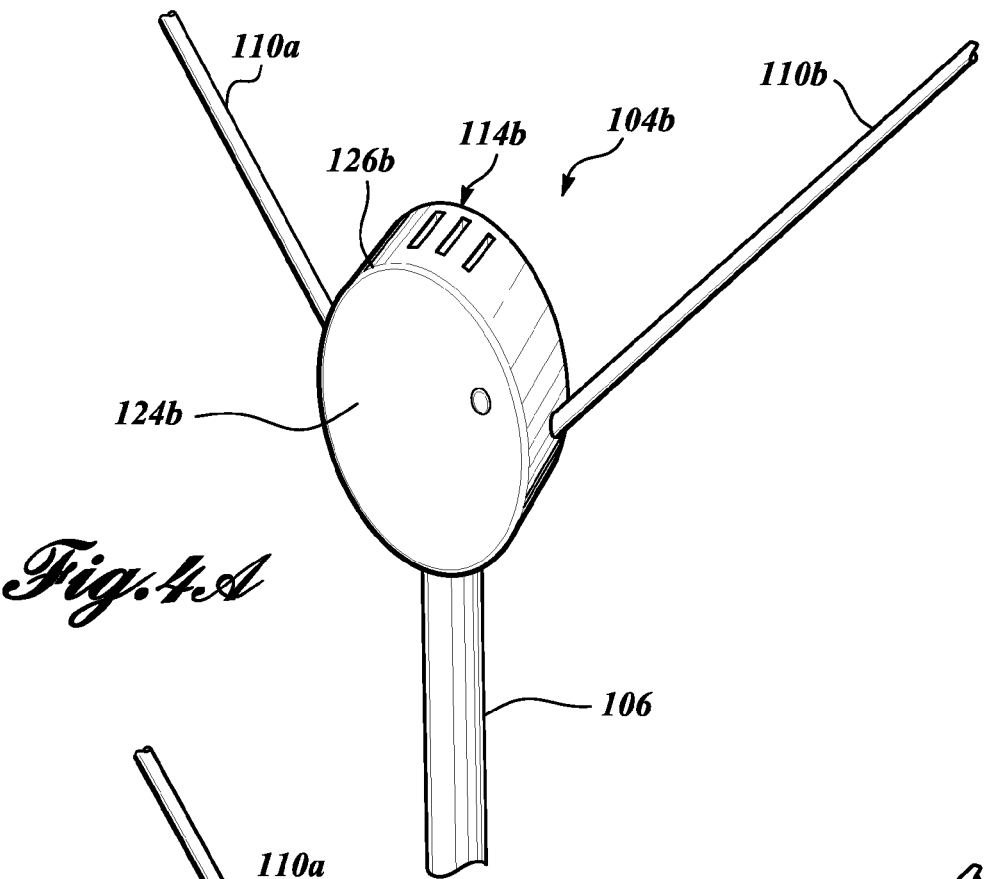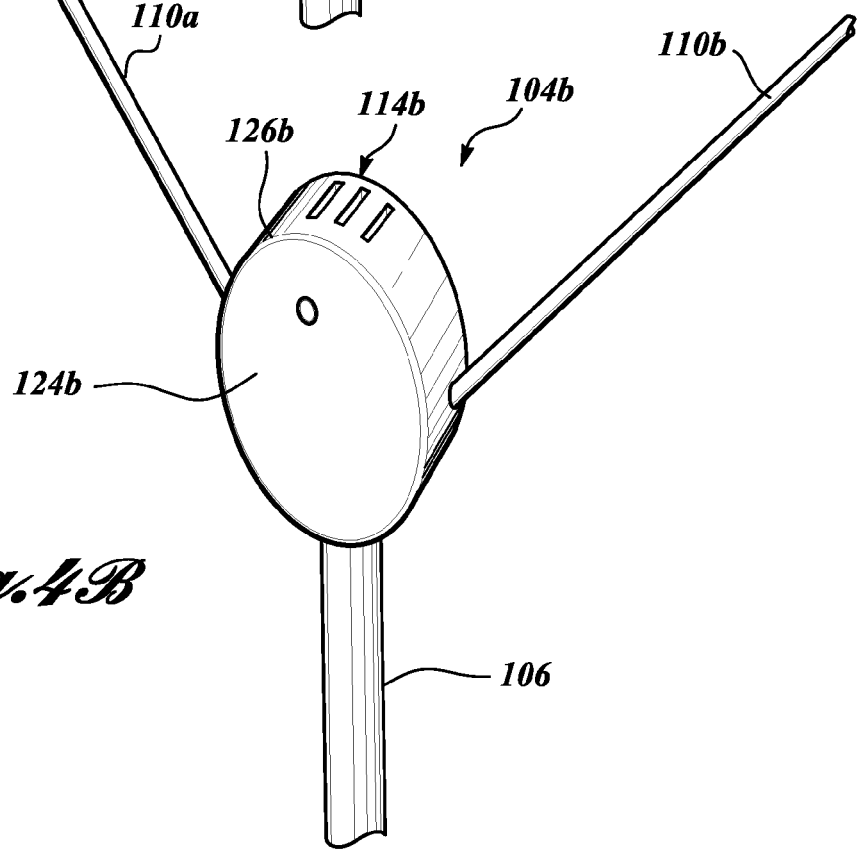

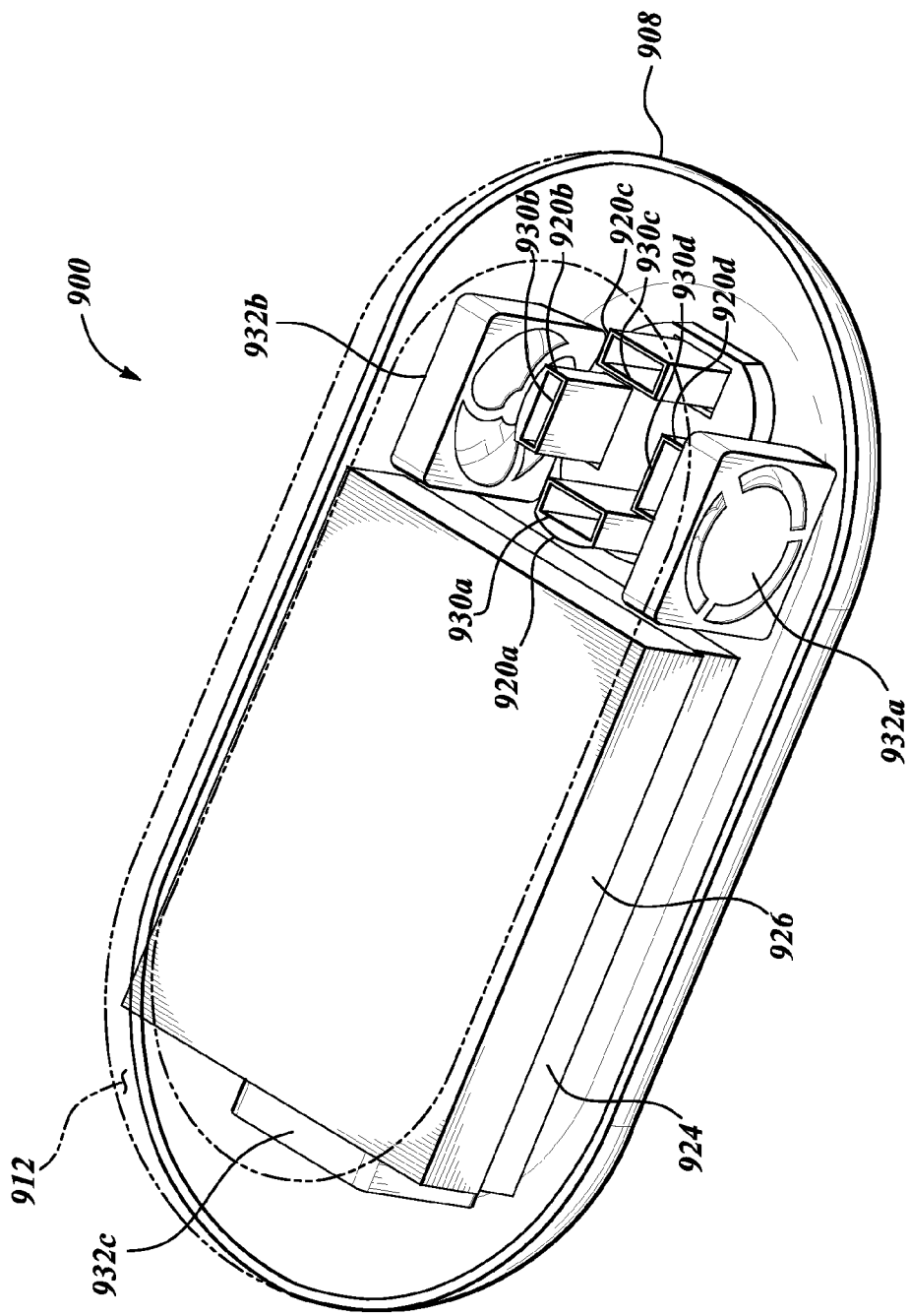

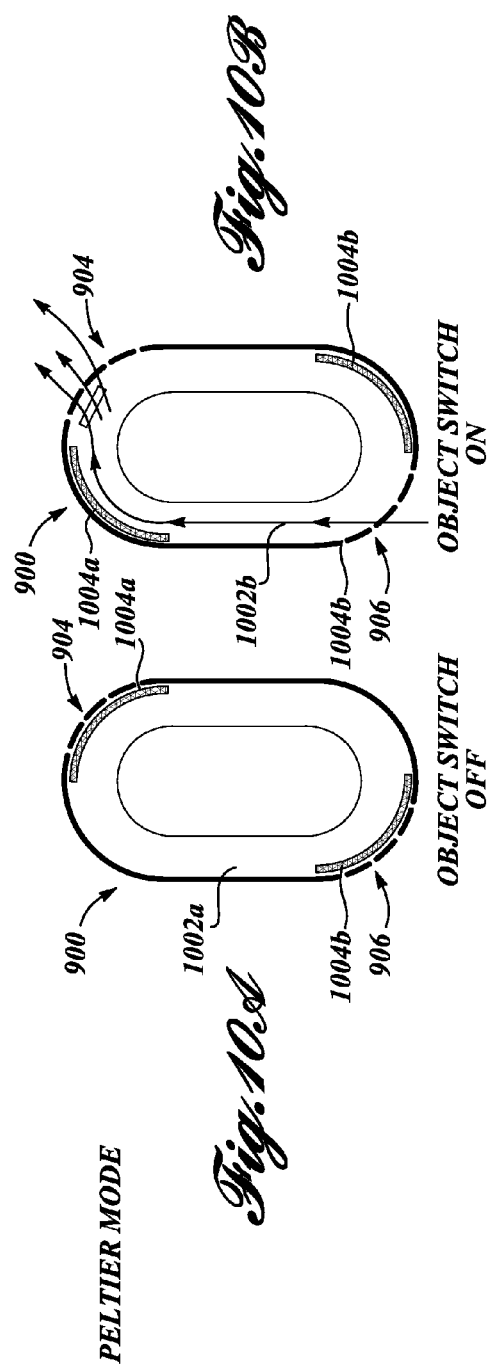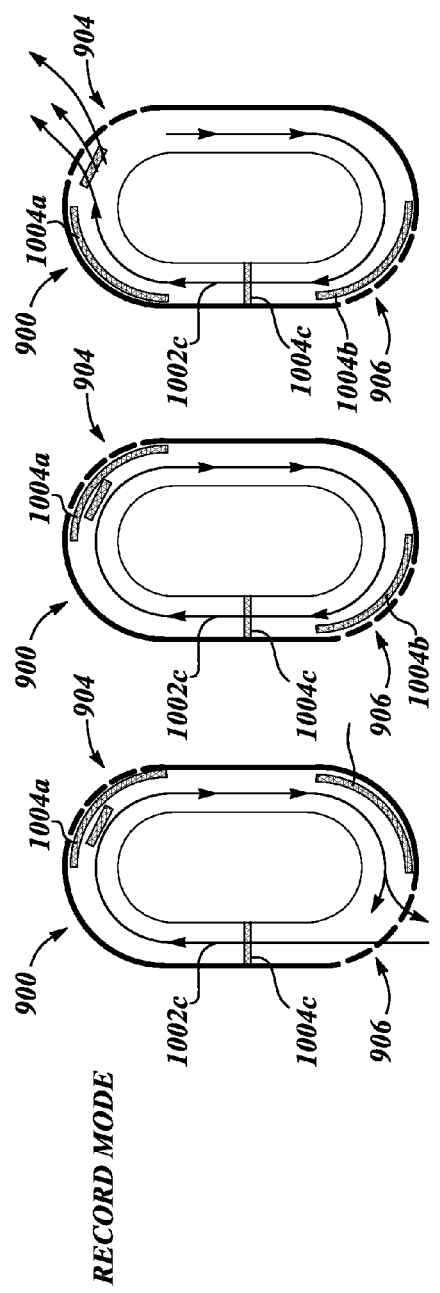

SYSTEMS, METHODS AND ARTICLES TO PROVIDE OLFACTORY SENSATIONS

BACKGROUND

Field

This disclosure generally relates to providing olfactory sensations to one or more users via a controlled system.

Description of the Related Art

All of our five sense act as messengers that deliver information to the brain, which then processes this information, causing us to respond in relatively predictable ways. Within the context of our sense of smell, all odors present themselves in specific chemical configurations, allowing humans to perceive a wide variety of distinct odors. Odor perception initiates in the nose, where the respective molecules are detected by a large family of olfactory receptors. Olfactory receptors have diverse protein sequences, and are assigned to subfamilies on the basis of sequence relationships. These observations formed the basis for research into the mechanisms underlying human odor perception, leading to the 2004 grant of the Nobel Prize in Physiology and Medicine to Linda B. Buck and Richard Axel.

However, even given the significant importance of our sense of smell, relatively little has been done to develop the apparent physiological value of this sense or to more thoroughly incorporate it into how humans experience the world around them on a daily basis. Although some systems and devices have been proposed for attempting to provide olfactory sensations to users, they have proven inadequate as mobile, personal, targeted and effective delivery systems that may be used to alter behavior. Some of these systems and devices are intended for personal use (see, for instance, U.S. Pat. Nos. 8,050,545, 8,032,014, 6,654,664 and 6,803,987), while other systems and devices are intended to provide olfactory sensations simultaneously to groups of people, for example people located in a common area such as a movie theater. One such system, known as "Smell-O-Vision", released odor during the projection of a film so that the viewer could "smell" what was happening in the movie. The technique was created by Hans Laube and made its only commercial appearance in the 1960 film Scent of Mystery. The process injected 30 odors into a movie theater's seats when triggered by the film's soundtrack. Smell-O-Vision did not work as intended. According to Variety, aromas were released with a distracting hissing noise and audience members in the balcony complained that the scents reached them several seconds after the action was shown on the screen. In other parts of the theater, the odors were too faint, causing audience members to sniff loudly in an attempt to catch the scent.

More recently, the Disneyland Resorts have made use of this idea in their 3-D films and other attractions. The Disney California attraction It's Tough to be a Bug releases an unpleasant odor coinciding with a stink bug on-screen, causing an audience reaction. Similarly, Soarin' Over California includes orange blossom, pine forest, and sea air fragrances as the scenery flies below the passengers.

Other attempts have included systems to enhance the video gaming experience, such as ScentScape, which provides background scents to complement the environment shown on the screen. As briefly noted above, many of these attempts have not proved adequate, being limited in one way or another.

New approaches that selectively automate, including more precisely control and remotely deliver desired scents, as well as coordinate audio and/or visual stimuli with olfactory sensations in order to deliver a physiological response, for personal and/or group use are desirable.

BRIEF SUMMARY

As described in more detail below, systems are provided which allow the portable, discrete delivery of olfactory stimuli with audio and/or visual signals, enhancing the impact on human and animal behavior, while minimizing the impact on those not targeted by the olfactory stimuli, and thereby significantly enhancing the overall sensory experience of the user. Advantageously, the system is configured to be portable, allowing the user to have the benefit of the system, on demand, in a wide variety of environments. The programming of the system can be activated by either a remote device such as a phone or other electronic equipment, or by the user. But without a willful choice by the user, odors will not be emitted from the device; this minimizes scent waste or pollution. The user may also limit the amount of odor released to the environment, to protect others from the stimuli, both by limiting the amount of odor that is released for scent, and also the amount of air that is filtered by the system and released to the environment. As noted above, as a complement to the programming control provided to the user, the system may also be configured to receive signals provided from a variety of devices in a remote manner, thereby allowing a third party to engage the user via olfactory stimuli in addition to audio and/or visual signals. The system may be used not only to enhance the overall sensory experience of the user, but, notably through the connection of the olfactory and auditory/visual signals, may be used to induce or enhance behavior change, altering physiological states. For instance, the system can deliver coffee vapor associated with music and visual imagery, e.g. a coffee cup, which will lead to greater states of alertness. Or the system can deliver chocolate vapor associated with images of chocolate, and promote satiety.

In summary, a system which provides one or more scent(s) is driven by scent specifications or sets of scent delivery sequences. The system may employ a variety of scent media carriers, for instance cartridges, which each carry a number of consumable scent media. The scent media may take the form of a scent wax, scented paper or scented powder. The system may employ a scent actuator to selectively release the scent from the consumable scent media. For example, the system may advantageously employ one or more Peltier devices. Such allows selective vaporization or aerosolization, e.g., by active heating, as well as selected active cooling, of the consumable scent media, providing more precise control of scent release as compared to conventional approaches.

The system selectively provides scents according to defined scent specifications or sets of scent delivery sequences. The scent specifications or sets of scent delivery sequences may specify specific scents by specific identifiers of values, or may generically specify scents, for instance based on positions on a scent media carrier where various scent media carriers may carry different sets of scent media from one another.

The system may employ a configurable circulation system, including various fluid flow paths or conduits, fans or other air movers, and/or valves. Such may be selectively controlled to provide scent to a scent port. Such may be selectively controlled to collect and return scent to a filter medium before exhausting to an ambient environment. Such may be selectively controlled to reuse or recycle scent, returning scent to the scent port. Such may even allow collection of scent from the environment, in lieu of the consumable scent media. One advantage of this system is that it allows a user to control delivery and minimize scent pollution, or amplify fidelity of the scent signal.

The system may take the form of a drive unit with an integral scent port, the drive unit selectively communicatably coupleable to a source of media content, such as a mobile communications device or media content player (commonly referred to as a media player). The system may optionally employ a pendant with a scent port, the pendant separate from the drive unit housing that holds the consumable scent media, scent actuators, and/or control subsystem. The pendant is selectively positionable by a user proximate the user's nose. The pendent may include a user operable element to allow the user to control system operation. The pendant may be coupled to the housing via one or more cables, which may include conduits, for instance a delivery conduit and a collection conduit. The cable may further include wires or optical fibers to provide communications via the drive unit. The drive unit may be wiredly, optically, or wirelessly coupled to one or more speakers, for example to provide sound thereto. Alternatively or additionally, the pendant may be wiredly, optically, or wirelessly coupled to one or more speakers, for example to provide sound thereto.

The drive unit may be wiredly, optically, or wirelessly communicatively coupled to a mobile communications device or media content player. The mobile communications device or media content player may provide audio (e.g., music, spoken word, MP3), video (e.g., MP4) and/or instructions to a control subsystem of the drive unit.

While generally described in terms of a personal use system, the system may take forms suitable for simultaneously or concurrently providing scent to multiple people, for example people occupying a common space such as a theater.

A portable scent delivery system may be summarized as including a housing having at least a scent generation chamber that at least in use holds scent media; a scent actuator controllably operable to cause release of one or more scents from the scent media in the scent generation chamber; a scent port that is operable to selectively release scents, if any, from the scent chamber via convection in response to at least one end user input; and a control subsystem communicatively coupled to control the scent actuator in response to a set of scent activation information which is part of a remotely generated scent experience package which also includes one or more sets of audio and/or image information.

The portable scent may further include a user actuatable control communicatively coupled to provide the at least one end user input to cause the scent port to selectively release scents via convection. The user actuatable control may be coupled to the housing. The control subsystem may be communicatively coupled to receive the scent activation information from a mobile communications device or media content player, and may cause release of the scents in a synchronization with audio and/or images specified by the audio and/or image information. The control subsystem may be communicatively coupled to receive the scent activation information from a mobile communications device or media content player, and may cause release of the scents in a synchronization with audio and/or images specified by the audio and/or image information and presented by the mobile communications device or media content player. The scent actuator may be controllably operable to release one or more scents in precisely controlled amounts at precisely controlled times. The scent port may be operable to release one or more scents in precisely controlled amounts at precisely controlled times. The set of scent activation information may be an integral part of the remotely generated scent experience package which may also include the one or more sets of audio and/or image information, and expires along with the remotely generated scent experience package.

A system operable to deliver scent may be summarized as including a housing; a receiver at least partially housed in the housing, the receiver sized and dimensioned to removably receive scent media carriers which carry a number of consumable scent media; and at least one Peltier device positioned at least proximate the receiver and selectively operable to actively heat and alternatively actively cool the consumable scent media of the scent media carrier while the scent media carrier is received by the receiver.

The system wherein the housing includes at least a first compartment, a second compartment, and a third compartment, the receiver located in the first compartment, may further include at least one filter, the at least one filter located in the second compartment, separate from the receiver which is located in the first compartment; and a control subsystem located in the third compartment.

The system may further include a first fan positioned in the housing and selectively operable to cause scent to move outwardly of the housing.

The system may further include a second fan positioned in the housing and selectively operable to draw scent inwardly back to the housing.

The system wherein the housing may include a scent mixing chamber and a filter chamber, the filter chamber separate from the scent mixing chamber and may be sized and dimensioned to hold filter medium, may further include a first valve positioned in the housing and selectively operable to control passage of scent from the scent mixing chamber to a configurable fluidly communicative conduit path; and a second valve positioned in the housing and selectively operable to control passage of scent to the filter chamber from the configurable fluidly communicative conduit path.

The system may further include at least a scent delivery conduit that provides fluid communication between the scent chamber and the scent port that in use releases scent to a user from the scent delivery conduit.

The system may further include at least a scent return conduit that provides fluid communication between the scent port and the filter chamber. The scent delivery and the scent return conduits may each be respective pieces of stretched neoprene tubing with an inner diameter of approximately 1.5 millimeters.

The scent delivery and the scent return conduits may form a scent circulation loop, and may further include a scent port valve in the scent circulation loop, the scent port valve selectively operable to control passage of scents via the scent port.

The system may further include a pendant having a scent port.

The system may further include a first cable that runs from the housing to the scent port, the first cable including at least a scent delivery conduit that provides fluid communication between the scent chamber and the scent port that in use releases scent to a user from the scent delivery conduit.

The first cable may further include at least a scent return conduit that provides fluid communication between the scent port and the filter chamber.

The system may further include a control subsystem; and a second cable communicatively coupleable to at least one of a mobile communications device or a media player to pass signals between the mobile communications device or the media player and the control subsystem of the system.

The system may further include a control subsystem; and a second cable communicatively coupleable to an audio source to pass signals between audio source and the control subsystem of the system. The first cable may include a number of wires to pass signals from the mobile communications device or the media player through the system to a number of speakers.

The pendant may include at least a first portion and a second portion, the second portion may be pivotally mounted to the first portion for rotation relative thereto; and may further include a control subsystem, the control subsystem communicatively coupled to control the at least one Peltier device, the control subsystem at least partially responsive to an orientation of the second portion of the pendant relative to the first portion of the pendant. The control subsystem may activate at least one fan in response to orientation of the second portion of the pendant relative to the first portion of the pendant.

The system may further include a touch sensor that senses human touch of at least a portion of the pendant; and a control subsystem, the control subsystem communicatively coupled to control the at least one Peltier device, the control subsystem at least partially responsive to human touch of the pendant.

The system may further include a motion sensor that senses movement of at least a portion of the pendant; and a control subsystem, the control subsystem communicatively coupled to control the at least one Peltier device, the control subsystem at least partially responsive to movement of the pendant.

The system may further include a control subsystem, the control subsystem communicatively coupled to control the at least one Peltier device.

The system may further include a control subsystem, the control subsystem communicatively coupled to control the at least one Peltier device, the control subsystem at least partially responsive to an orientation of the at least a portion of the housing. The control subsystem may activate at least one fan in response to an orientation of at least a portion of the housing.

The system may further include a touch sensor that senses human touch of at least a portion of the housing; and a control subsystem, the control subsystem communicatively coupled to control the at least one Peltier device, the control subsystem at least partially responsive to human touch of the at least portion of the housing.

The system may further include a motion sensor that senses movement of at least a portion of the housing; and a control subsystem, the control subsystem communicatively coupled to control the at least one Peltier device, the control subsystem at least partially responsive to movement of the at least portion of the housing.

The system may further include a control subsystem, the control subsystem at least partially responsive to control the at least one Peltier device based on at least one of images or information displayed on a display of a mobile communications device or the media player to which the system is communicatively coupled.

The system may further include a control subsystem, the control subsystem communicatively coupled to control the at least one Peltier device, the control subsystem at least partially responsive to control the at least one Peltier device based on user selections of user selectable icons or information displayed on a display of a mobile communications device or the media player to which the system is communicatively coupled.

The system may further include a control subsystem, the control subsystem communicatively coupled to control the at least one Peltier device, the control subsystem at least partially responsive to control the at least one Peltier device based on images captured by an image sensor of a mobile communications device or the media player to which the system is communicatively coupled.

The system may further include at least one of the scent media carriers, which carries at least two consumable scent media in the form of a wax substrate with a respective lipophillic scent.

The system may further include a heat sink with a plurality of heat transfer projections extending therefrom, the heat sink thermally conductively coupled to the at least one Peltier device.

The system may further include a microcontroller housed by the housing; and a power supply subsystem including a first stage coupled to supply current to the microcontroller at a first voltage and a second stage coupled to supply current to the at least one Peltier device at a second voltage, different from the first voltage.

The system may further include a transceiver housed by the housing and operable to provide communications with at least one of a mobile communications device or a media player.

The system may further include a transmitter housed by at least one of the housing or a pendant and operable to provide communications with a number of speakers.

A method of operating a system to deliver scent may be summarized as including selectively activating by a control subsystem at least one Peltier device positioned at least proximate a receiver that removably receives scent media carriers which carry a number of consumable scent media to actively heat selected ones of the consumable scent media of the scent media carrier while the scent media carrier is received by the receiver; and selectively activating by the control subsystem at least one Peltier device positioned at least proximate the receiver that removably receives scent media carriers which carry the number of consumable scent media to actively cool the consumable scent media of the scent media carrier while the scent media carrier is received by the receiver.

The method may further include operating a first fan by the control subsystem to cause scent to move outwardly of a housing that houses at least the at least one Peltier device.

The method may further include operating a second fan by the control subsystem to draw scent inwardly back to the housing.

The method may further include selectively operating by the control subsystem a first valve operable to control passage of scent from a scent mixing chamber to a configurable fluidly communicative conduit path; and selectively operating by the control subsystem a second valve operable to control passage of scent to a filter chamber from the configurable fluidly communicative conduit path.

The method may further include fluidly communicatively coupling a scent mixing chamber of the housing to a scent port via a scent delivery conduit that provides fluid communication between the scent mixing chamber and the scent port that in use releases scent to a user from the scent delivery conduit.

The method may further include fluidly communicatively coupling the scent port to a filter chamber of the housing via a scent return conduit that provides fluid communication between the scent port and the filter chamber.

The scent delivery and the scent return conduits may form at least a portion of a scent circulation loop, and further include selectively controlling a scent port valve in the scent circulation loop by a control subsystem to control passage of scents via the scent port.

The method may further include communicatively coupling the control subsystem of the system to at least one of a mobile communications device or a media player to pass signals between the mobile communications device or the media player and the control subsystem of the system.

The method may further include wiredly or wirelessly communicatively coupling the control subsystem of the system to at least one of a mobile communications device or a media player to pass audio signals between the mobile communications device or the media player and the control subsystem of the system.

The method may further include controlling by the control subsystem operation of the at least one Peltier device at least partially responsive to at least one of a position or an orientation of at least a portion of a drive unit of the system.

The method may further include sensing a human touch of at least a portion of a drive unit of the system; and controlling by the control subsystem at least one of the at least one Peltier device or at least one fan at least partially responsive to human touch.

The method may further include sensing a movement of at least a portion of a drive unit of the system; and controlling by the control subsystem at least one of the at least one Peltier device or at least one fan at least partially responsive to the sensed movement of the at least portion of the drive unit.

The method may further include controlling by the control subsystem operation of the at least one Peltier device at least partially responsive to at least one of a position or an orientation of a second portion of a pendant relative to a first portion of the pendant.

The method may further include controlling by the control subsystem operation of the at least one fan at least partially responsive to at least one of a position or an orientation of a second portion of a pendant relative to a first portion of the pendant.

The method may further include sensing a human touch of at least a portion of a pendant; and controlling by the control subsystem at least one of the at least one Peltier device or at least one fan at least partially responsive to human touch of the pendant.

The method may further include sensing a movement of a pendant; and controlling by the control subsystem at least one of the at least one Peltier device or at least one fan at least partially responsive to the movement of the pendant.

The method may further include controlling by the control subsystem operation of at least one of the at least one Peltier device or the at least one fan based on at least in part on at least one of images or information displayed on a display of a mobile communications device or the media player to which the system is communicatively coupled.

The method may further include controlling by the control subsystem operation of at least one of the at least one Peltier device or the at least one fan based at least in part on user selections of user selectable icons or information displayed on a display of a mobile communications device or the media player to which the system is communicatively coupled.

The method may further include controlling by the control subsystem operation of at least one of the at least one Peltier device or the at least one fan based at least in part on images captured by an image sensor of a mobile communications device or the media player to which the system is communicatively coupled.

A system operable to deliver scent may be summarized as including a housing having at least a scent generation chamber and a filter chamber, the scent generation chamber sized and dimensioned to removably receive scent media carriers which carry a number of consumable scent media, and the filter chamber sized and dimensioned to hold filter medium; a scent actuator selectively operable to cause release of respective scents into the scent generation chamber by respective ones of a number of scent media; and a configurable fluid circulation path, the configurable fluid circulation path comprising: a number of conduits fluidly communicatively coupled as a configurable fluidly communicative conduit path; an inlet valve selectively operable to control passage of scent from the scent generation chamber to a portion of the configurable fluidly communicative conduit path; an outlet valve positioned in the housing and selectively operable to control passage of scent to the filter chamber from a portion of the configurable fluidly communicative conduit path; and a scent port that in use releases scent to a user from the configurable fluid circulation path. The number of conduits fluidly communicatively coupled as the configurable fluidly communicative conduit path may include a delivery conduit that provides a first fluid communication path between the scent generation chamber and the scent port; and a return conduit that provides a second fluid communication path between the scent port and the filter chamber.

The system may further include a first fan positioned and selectively operable to cause scent to move from the scent mixing chamber into the configurable fluid circulation path.

The system may further include a second fan positioned and selectively operable to create a lower pressure in the configurable fluid circulation path on a downstream side of the scent portal relative to a pressure in the configurable fluid circulation path on an upstream side of the scent portal.

The system may further include a control subsystem, the control subsystem communicatively coupled to control operation of at least one of the first or the second fans in response to at least one user input. The control subsystem may further activate at least one Peltier device housed in the housing, in response to the at least one user input.

The system may further include a pendant having the scent port. The pendant may include at least a first portion and a second portion, the second portion may be pivotally mounted to the first portion for rotation relative thereto, and the control subsystem may activate at least one of the first or the second fans in response to an orientation of the second portion of the housing relative to the first portion of the housing.

The system may further include a first cable that runs from the housing to the scent port, the first cable including at least a scent delivery conduit that provides fluid communication between the scent chamber and the scent port, the scent delivery conduit which forms at least a portion of the configurable fluid circulation path. The configurable fluid circulation path may include a scent port valve selectively operable to control passage of scents via the scent port. The configurable fluid circulation path may include an intermediary valve selectively operable to regulate passage of scent from the return conduit to the delivery conduit of the fluidly communicative conduit path. The number of conduits fluidly communicatively coupled as a configurable fluidly communicative conduit path may be formed by inner surfaces of the housing. The number of conduits fluidly communicatively coupled as a configurable fluidly communicative conduit path may be formed by at least one inner surface of the housing, the at least one inner surface may have a rough texture to induce a turbulent flow.

A method of operation in a scent delivery system which includes a housing having at least a scent generation chamber and a filter chamber, the scent generation chamber sized and dimensioned to removably receive scent media carriers which carry a number of consumable scent media, and the filter chamber sized and dimensioned to hold filter medium, may be summarized as including operating a scent actuator by a control subsystem to selectively cause release of respective scents into the scent generation chamber by respective ones of a number of scent media; operating an inlet valve by the control subsystem to selectively control passage of scent from a scent generation chamber to a portion of the configurable fluidly communicative conduit path; operating an outlet valve by the control subsystem to selectively control passage of scent to a filter chamber from a portion of the configurable fluidly communicative conduit path; and allowing scent to be released from the configurable fluid circulation path to a user via a scent port. Operating an inlet valve by the control subsystem to selectively control passage of scent from a scent generation chamber to a portion of the configurable fluidly communicative conduit path may include operating the inlet valve to selectively control passage of scent via a delivery conduit that may provide a first fluid communication path between the scent generation chamber and the scent port; and operating an outlet valve by the control subsystem to selectively control passage of scent to a filter chamber from a portion of the configurable fluidly communicative conduit path may include operating the outlet valve to selectively control passage of scent via a return conduit that may provide a second fluid communication path between the scent port and the filter chamber.

The method may further include operating a first fan to cause scent to move from the scent mixing chamber into the configurable fluid circulation path.

The method may further include operating a second fan to create a lower pressure in the configurable fluid circulation path on a downstream side of the scent portal relative to a pressure in the configurable fluid circulation path on an upstream side of the scent portal. The first and the second fans may be operated at least partially concurrently.

The method may further include receiving at least one signal by the control subsystem indicative of a user input; and controlling operation of at least one of the first or the second fans in response to the user input.

The scent actuator may include at least one Peltier device, and may further include receiving at least one signal by the control subsystem indicative of a user input; and controlling operation of at least one Peltier device in response to the user input. The scent delivery system may include a pendant having the scent port, and receiving at least one signal by the control subsystem indicative of a user input includes receiving at least one signal indicative of the user input from the pendant.

The method may further include operating a scent port valve to selectively control passage of scents via the scent port.

The method may further include operating an intermediary valve to selectively regulate passage of scent from the return conduit to the delivery conduit of the fluidly communicative conduit path.

A system may be summarized as including a housing; a receiver at least partially housed in the housing, the receiver sized and dimensioned to removably receive scent media carriers which carry a number of consumable scent media; a scent actuator selectively operable to cause release of respective scents by respective ones of the consumable scent media; and a user input element having a first portion and a second portion, the second portion movable with respect to the first portion; a control subsystem, the control subsystem communicatively coupled to control the scent activation device, the control subsystem at least partially responsive to at least one of a position or an orientation of the second portion of the user input element relative to the first portion of the user input element. The second portion may be pivotally mounted to the first portion for rotation relative thereto. The user input element may take the form of a pendant.

The system may further include a first cable that runs from the housing to a scent port, the first cable including at least a scent delivery conduit that provides fluid communication between the housing and the scent port that in use releases scent to a user from the scent delivery conduit. The first cable may further include at least a scent return conduit that provides fluid communication between the scent port and the housing. The scent delivery and the scent return conduits may each be respective pieces of stretched neoprene tubing with an inner diameter of approximately 15 millimeters.

The scent delivery and the scent return conduits may form a scent circulation loop, and may further include a valve in the scent circulation loop, the valve selectively operable to control passage of scents via the scent port.

The system may further include a control subsystem; and a second cable communicatively coupleable to at least one of a mobile communications device or a media player to pass signals between the mobile communications device or the media player and the control subsystem of the system. The first cable may include a number of wires to pass signals from the mobile communications device or the media player through the system to a number of speakers. The scent actuator may include at least one Peltier device.

A system may be summarized as including a receiver sized and dimensioned to removably receive scent media carriers, each of the scent media carriers which carry a plurality of consumable scent media positioned at a number of defined spatial positions on the respective scent media carrier; a scent actuator selectively operable to cause release of respective scents by respective ones of the scent media carried by one of the scent media carriers while the scent media carrier is received by the receiver; and a control subsystem communicatively coupled to control the scent actuator at least partially responsive to a set of scent activation information that species a temporal sequence of generic values that generically specify respective ones of scent media irrespective of the which specific scent media are carried on any particular ones of the scent media carriers. The set of scent activation information may specify, a start time and at least one of a finish time or a duration for each of the generic values, and the control subsystem may be communicatively coupled to control the scent actuator at least partially responsive to the start time and the at least one of a finish time or a duration for each of the generic values. The generic values may specify a relative position of the scent media on the respective scent media carrier, and the control system may activate selected ones of a plurality of Peltier devices based on a respective position of the Peltier device with respect to the scent media carrier. The generic values may specify a musical characteristic. The control system may detect musical characteristics in music and may synchronize activation of selected ones of a plurality of Peltier devices with the respective musical characteristic specified by the set of scent activation information. The generic values may specify an emotional state.

The system may further include at least one communications port via which the set of scent activation information is received from a remote device. The set of scent activation information may be formatted as a Musical Instrument Digital Interface file.

A system may be summarized as including at least one processor; and at least one nontransitory processor-readable media that stores at least one of processor-executable instructions or data, that execution of which causes the at least one processor to present a user interface operable by a user to generated a set of scent activation information in a standard format that species a temporal sequence of generic values that generically specify respective ones of scent media irrespective of the which specific scent media are carried on any particular ones of the scent media carriers. The set of scent activation information may specify a start time and at least one of a finish time or a duration for each of the generic values. The generic values may specify a relative position of the scent media on the respective scent media carrier. The generic values may specify a musical characteristic. The set of scent activation information may specify synchronization information to synchronize scent delivery with at least one piece of music. The generic values may specify an emotional state.

The system may further include providing the set of scent activation information remotely to a scent delivery system. The set of scent activation information may be formatted as a Musical Instrument Digital Interface file.

A scent cartridge may be summarized as including a substrate; a plurality of temperature activated scent media carried by the substrate, the temperature activated scent media each selectively activatable to release a respective scent and to stop releasing the respective scent, the scents released by at least two of the temperature activated scent media different from one another; and at least one alignment structure, the scent cartridge sized to be at least partially received in a housing, the alignment structure cooperatively interfacing with a complimentary alignment structure of the housing to at least one of position or orient the temperature activated scent media in a defined position or orientation with respect to a set of activation elements in the housing.

The temperature activated scent media may be spatially distributed on a planar surface of the substrate. The temperature activated scent media may lie in a plane on the planar surface of the substrate. The temperature activated scent media may be spatially distributed on a planar surface of the substrate positioned to thermally conductively couple to a respective one of the activation elements of the set of activation elements. The scent cartridge may further include a metallic foil in physical contact with at least some of the temperature activated scent media, the metallic foil thermally conductively coupling the temperature activated scent media to respective ones of the activation elements when the scent cartridge is at least partially received in the housing. At least four of the activated scent media may be spatially distributed on a planar surface of the substrate in an ordered array of rows and columns, a respective scent releasable by each of the temperature activated scent media being different from one another. A respective major axis of each of the temperature activated scent media may be arranged with the respective major axis extending perpendicularly to the planar surface of the substrate. The temperature activated scent media may be spatially distributed on a planar surface of the substrate positioned to thermally conductively couple to a respective one of the activation elements of the set of activation elements. The scent cartridge may further include a metallic foil in physical contact with at least some of the temperature activated scent media, the metallic foil thermally conductively coupling the temperature activated scent media to respective ones of the activation elements when the scent cartridge is at least partially received in the housing. At least four of the temperature activated scent media may be spatially circumferentially arrayed about a planar surface of the substrate. The substrate may be circular and there may be four of the temperature activated scent media spatially circumferentially array 90 degrees apart about a center of the substrate. The scent cartridge may further include a respective piece of metallic foil overlying each of the temperature activated scent media, and each of the pieces of metallic foil may be spaced radially inwardly with respect to the respective temperature activated scent media which the metallic foil overlies. The scent cartridge may further include a metallic foil which may overly at least some of the temperature activated scent media. The temperature activated scent media may take the form of a wax impregnated with a respective volatile, lipophillic, or oil-based scent substance. The substrate may form at least a portion of a plug, and may further include a securement structure to releasably secure the scent cartridge in the housing.

An article for use in providing scent experiences via a scent delivery device may be summarized as including a nontransitory processor-readable medium that stores processor executable instructions which specify a scent track in the form of a sequence of activation for each of at least some of a plurality of scent media, including information indicative of a duration of activation for each of the at least some of the plurality of scent media.

The scent track may include information indicative of a start time for each of the at least some of the plurality of scent media. The scent track may include information indicative of an end time for each of the at least some of the plurality of scent media. The scent track may include information indicative of a period after a start time during which the respective scent media is to be activated. The scent track may include information indicative of an end time for each of the at least some of the plurality of scent media specified as an offset from the respective start time. The scent track may include information that specifies a cool down period for each of the at least some of the plurality of scent media. The scent track may include information that specifies an active cool down period for each of the at least some of the plurality of scent media, during which the respective scent media is actively cooled. The scent track may include information that generically maps transitions in at least one of audio or video presentation to classes of scents. The scent track may include information that specifies classes of scents, the classes of scents mapped to positions of scent media on the substrate rather than to specific scents. The scent track may include information that specifies positions of scent media on the substrate rather than specific scents.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 2A is a front elevational view of a user with a portion of the system of FIG. 1, showing a pendant hanging proximate the user's chest.

FIG. 2B is left side elevational view of the user of FIG. 2A with the pendant raised to be proximate the user's nose.

FIG. 4A is a front isometric view of a pendant according to one illustrated embodiment, showing a portion of the pendant rotated into an OFF position to prevent delivery of scent from a scent port of the pendant.

FIG. 4B is a front isometric view of the pendant of FIG. 4A, showing the portion of the pendant rotated into an ON position, to cause delivery of scent from the scent port of the pendant.

FIG. 9E is a top, right, rear isometric view of the system of FIG. 9A with the housing shown as transparent to illustrate components housed in the housing, according to one illustrated embodiment.

FIG. 10A is a schematic diagram of the system of FIGS. 9A-9G showing a flow path configuration in an OFF state, according to one illustrated embodiment.

FIG. 10B is a schematic diagram of the system of FIGS. 9A-9G showing a flow path configuration in an ON state in an active scent generation mode and a direct delivery configuration, according to one illustrated embodiment.

FIG. 10 is a schematic diagram of the system of FIGS. 9A-9G showing a flow path configuration in an ON state in a passive scent sampling mode and a record scent configuration, according to one illustrated embodiment.

FIG. 10D is a schematic diagram of the system of FIGS. 9A-9G showing a flow path configuration in an ON state in a passive scent sampling mode and a hold scent configuration, according to one illustrated embodiment, according to one illustrated embodiment.

FIG. 10E is a schematic diagram of the system of FIGS. 9A-9G showing a flow path configuration in an ON state in a passive scent sampling mode and a release scent configuration, according to one illustrated embodiment.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with microcontrollers, Peltier devices, power supplies such as DC/DC converters, wireless radios (i.e., transmitters, receivers or transceivers), computing systems including client and server computing systems, and networks (e.g., cellular, packet switched), as well as other communications channels, have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

System to Delivery Scent or Olfactory Sensation

Figure 1:
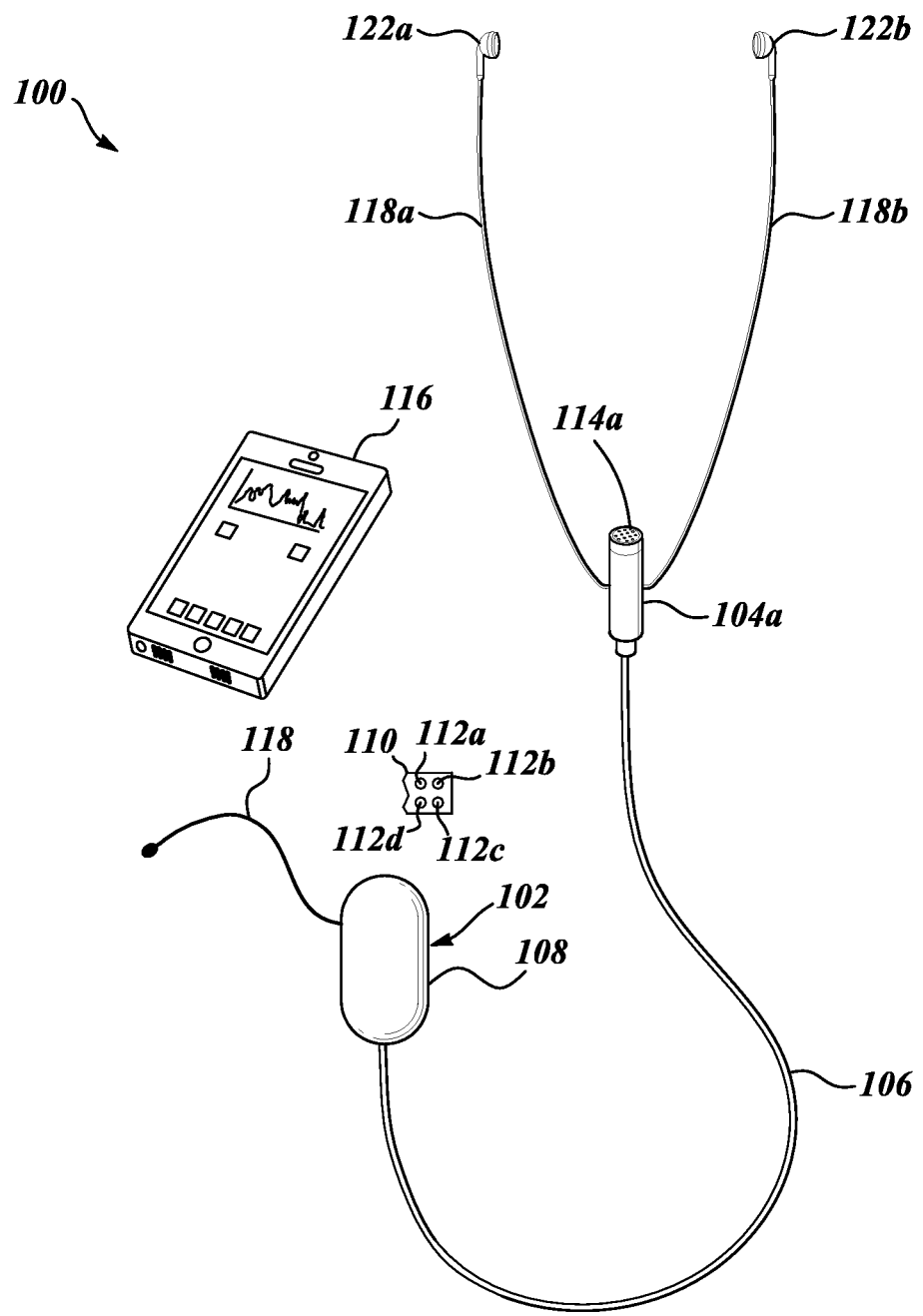
FIG. 1 is an isometric view of a system operable to deliver scent or olfactory sensation in a personalized form that includes a drive unit, pendant, and cables, according to one illustrated embodiment.

FIG. 1 shows a system 100 operable to deliver scent or olfactory sensation, according to one illustrated embodiment. In particular, FIG. 1 shows the system 100 in a personalized form, for delivering scent or olfactory sensation to individual users (i.e., scent consumers).

The system 100 includes a drive unit 102 and optionally a pendant 104a coupled to the drive unit 102 via one or more cables 106 (one shown). As described in detail herein, the drive unit 102 includes a housing 108 that houses many of the primary components of the drive unit 102, and which removably receives scent carriers 110 which carry scent media 112a-112d (four shown, collectively 112). Also as described in detail herein, the pendant 104a includes one or more scent ports 114a that provide scent to a user. Additionally as described in detail herein, the cable(s) 106 provide a configurable fluidly communicative path between the drive unit 102 and the scent port(s) 114a, for example in the pendant 104a. The cables 106 may also optionally provide an information communication path (e.g., wires, optical fiber) between the drive unit 102 and the pendant 104a.

Various components in the drive unit 102 may optionally be removably communicatively coupled to a mobile communications device (e.g., smart phone) or media content player (e.g., MP3 player, IPOD®, tablet computer, netbook computer, laptop computer) 116. The mobile communications device or media content player 116 typically does not constitute part of the system 100. The components of the drive unit 102 may be physically communicatively coupleable to the mobile communications device or media content player 116 via one or more cables 118 which include wires and/or optical fibers. Alternatively or additionally, various components of the drive unit 102 may be wirelessly communicatively coupleable to the mobile communications device or media content player 116 via one or more radios (i.e., wireless transmitters, receivers, and/or transceivers).

The pendant 104a may be physically coupled to various components of the drive unit 102. For example, one or more cables 106 may provide one or more fluidly communicative paths or conduits between the drive unit 102 and scent port(s) 114a which, as indicated above, may be located in the pendant 104a. The cable(s) 106 may additionally provide one or more information (e.g., instructions, data) signal paths (e.g., wired, optical) between the drive unit 102 and the pendant 104a. The optional pendant 104a is typically coupled to one or more tensile members which may take the form of cables 118a, 118b (collectively 118), or alternatively strings or wires which allow the pendant to be suspended on a body of the user. For instance, as best illustrated in FIG. 2A, the pendant 104a may be suspended proximate a chest 120a of a user 120 when not in active use. Employing a pendant 104a that is separate from the drive unit 102 allows heavier components to be separated from the pendant 104a. Such facilitates a positioning of scent ports 114a located in the pendant 104a proximate a nose 120b of the user 120 during active use, such as illustrated in FIG. 2B.

Returning to FIG. 1, the system 100 may optionally be communicatively coupled to, or alternatively include, one or more speakers 122a, 122b (collectively 122, two shown). Speakers 122 may take any of a large variety of forms, for example ear buds, ear headphones or over ear headphone speakers, which may or may not have open backs. The type of speaker, or even the existence of speakers 122 should not be considered limiting. As illustrated in FIG. 1, the speakers 122 may be physically coupled to the pendant 104a via one or more cables 118a, 118b. These cables 118 may include wires or optical fibers to supply signals to the speakers 122. Alternatively, the speakers 122 may be wireless coupled to the pendant 104a, or directly to the drive unit 102 via one or more radios (i.e., wireless transmitters, receivers and/or transceivers).

Figure 3A:
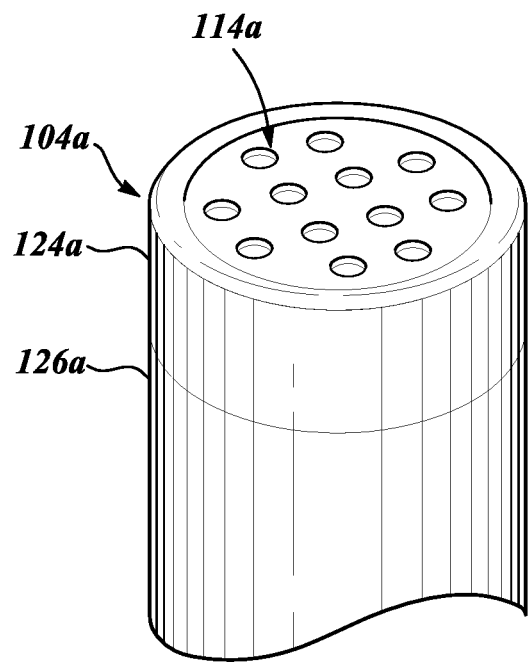
FIG. 3A is a top isometric view of a portion of the pendant of FIGS. 2A and 2B, showing a scent port in an open position to deliver scent therefrom.
Figure 3B:
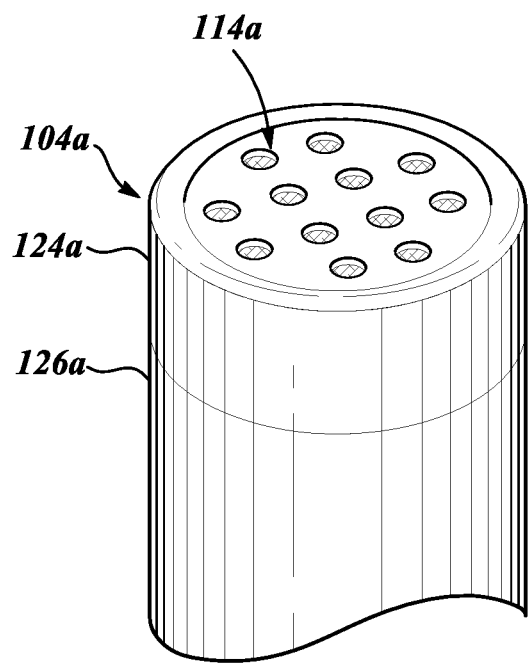
FIG. 3B is a top isometric view of the portion of the pendant of FIG. 3A, showing the scent port in a closed position to prevent delivery of scent therefrom.

FIG. 3A shows part of the pendant 104a of FIGS. 2A and 2B, illustrating the scent port(s) 114a in an open position to deliver scent therefrom. FIG. 3B shows the part of the pendant 104a of FIG. 3A, illustrating the scent port(s) 114a in a closed position to prevent deliver of scent therefrom. Notable, a first portion 124a of the pendant 104a is moveable with respect to a second portion 126a of the pendant 104a. In the embodiment of FIGS. 3A and 3B, the first portion 124a is pivotally or rotatable with respect to the second portion 126a. In a first open position (FIG. 3A) the scent port(s) 114a and/or one or more valves may be open, while in a second closed position (FIG. 3B) the scent port(s) 114a and/or one or more valves may be closed. As described in detail herein, the pendant 104a may include a sensor or switch (not shown) that detects a position, orientation or movement of the pendant 104a or portion(s) (e.g., first and/or second portions 124a, 124) thereof, and in response provides control signals to control operation of various components of the system 100, including the drive unit 102.

FIG. 4A shows a pendant 104b according to one illustrated embodiment, illustrating a first portion 124b of the pendant 104b rotated into an OFF position with respect to a second portion 126b of the pendent 104b to prevent delivery of scent from one or more scent port(s) 114b of the pendant 104b. FIG. 4B shows the pendant 104b of FIG. 4A, illustrating the first portion 124b of the pendant rotated into an ON position with respect to the second portion 126b of the pendant 104b, to cause delivery scent from the scent port(s) 114b of the pendant 114b. As previously stated, the pendant 114b may include one or more sensors or switches that detect a position, orientation or movement of the pendant 104b or portion(s) (e.g., first and/or second portions 124b, 126b) thereof, and in response provides control signals to control operation of various components of the system 100, including the drive unit 102.

FIGS. 5A-5E show a drive unit 102 according to one illustrated embodiment, which includes a housing 108 that houses many of the components of the drive unit 102.

The housing 108 may take any of a large variety of shapes, and is primarily intended to provide environmental protection to the various components of the drive unit 102 that are housed in the housing. The shape of the housing 108 should not be considered limiting. Likewise, the housing 108 may be constructed of a large variety of materials. For example, the housing 108 may be formed of metal, such as aluminum. The metal may be folded, welded, and/or machined. Alternatively, the housing 108 may be formed of one or more plastics, for example an ABS or polycarbonate plastic. The plastic may be injection molded or vacuum molded to form the housing 108. The type of material or process employed to form the housing 108 from the material should not be considered limiting.

The housing 108 may have a user removable cover (not shown), for example to allow the user to service one or more components of the drive unit 102. Alternatively, the housing 108 may prevent or deter user access to the internal components of the drive unit 102. The housing 108 may include a number of vents 127 to allow cooling via convective heat transfer.

The housing 108 of the drive unit 102 includes a number of ports.

For example, the housing 108 includes a scent carrier receiver port 128 to removably receive scent media carriers 110 (FIG. 1) which carry consumable scent media 112 (FIG. 1) into a scent carrier receiver 130. The scent carrier receiver port 128 may comprise a slot sized and dimensioned to receive the sent media carriers 110. The slot may, for instance, be similar in structure, size and/or dimension to structures used to removably receive SD cards and similar non-volatile media in various consumer electronics devices. The scent carrier receiver 130 may take the form of a frame of similar alignment structure which positions and/or orients a received scent carrier with respect to one or more scent actuators (e.g., Peltier devices discussed below). The scent carrier receiver 130 may include an ejection mechanism operable to selectively eject scent carriers 110 from the scent carrier receiver 130 via the scent carrier receiver port 128. The ejection mechanism may be similar or even identical to ejection mechanisms employed with SD card receivers found on many consumer electronics devices.

For example, one or more optional pendant cable ports 132 may allow coupling of a cable 106 (FIG. 1) (e.g., a pendant cable) to the drive unit 102. In particular the pendant cable port 132 may allow coupling of one or more fluidly communicative conduits between the drive unit 102 and optional pendant 104a, 104b (collectively 104) (FIG. 1).

The pendant cable port 132 may additionally allow coupling of one or more wires or optical fibers between the drive unit 102 and optional pendant 104. The wires or optical fibers may carry signals. For example, the wires or optical fibers may carry signals from one or more sensors or switches located in the pendant 104 to the drive unit 100, for instance signals indicative of user input(s), such as an ON or OFF condition or state. Additionally or alternatively, the wires or optical fibers may carry signals from or via the drive unit to the pendant 104 encoding audio information, for example audio signals to drive speakers 122.

As a further example, one or more optional cable ports 134 may allow selective removable coupling of the drive unit 102 with various mobile communications devices or media content players 116 (FIG. 1), for example via a cable 118 (FIG. 1). Such allows transfer of information and/or data between the drive unit 102 with various a mobile communications devices or media content players 116. For example, such allows downloading of defined scent specifications or sets of scent delivery sequences to the drive unit from, or via, the mobile communications devices or media content players 116. Also for example, such allows downloading of media content to the drive unit from, or via, the mobile communications devices or media content players 116. The defined scent specifications or sets of scent delivery sequences and/or media content may reside on the mobile communications devices or media content players 116, for example being created on and/or stored on the mobile communications devices or media content players 116. The defined scent specifications or sets of scent delivery sequences and/or media content may be passed by the mobile communications devices or media content players 116 from some other source, for example being created on and/or stored on a user computing device or server computing device (e.g., Web portal) as discussed further herein. Thus, the mobile communications devices or media content players 116 may serve as pass through devices for defined scent specifications or sets of scent delivery sequences and/or media content. While illustrated as a wired or optical port, the one or more optional cable ports 134 may be implemented as wireless ports (e.g., radio).

Figure 5A:
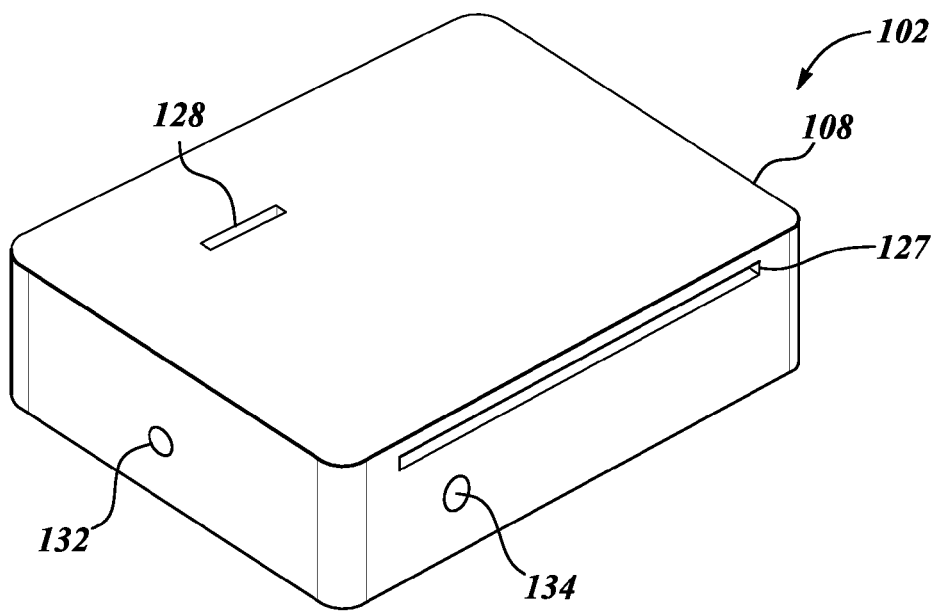
FIG. 5A is an isometric view of an exterior of a drive unit showing a housing of the drive unit, according to one illustrated embodiment, which houses many of the components of the drive unit.
Figure 5B:
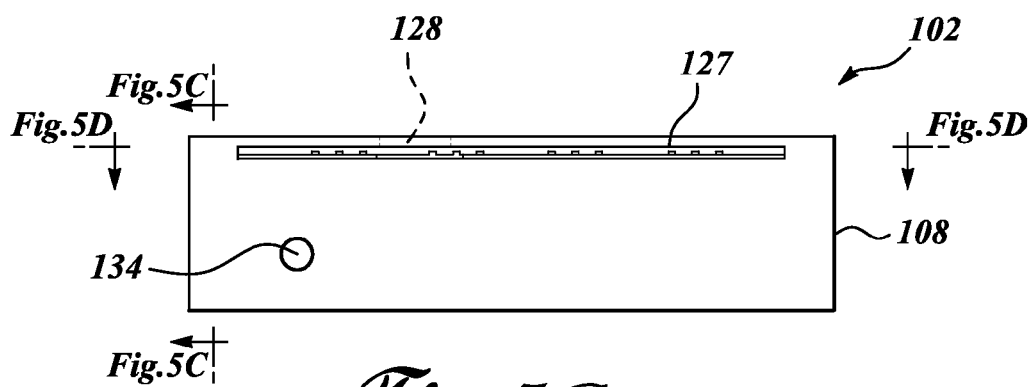
FIG. 5B is a side elevational view of the drive unit of FIG. 5A, illustrating a slot sized and dimensioned to removably receive scent media carriers which carry consumable scent media.
Figure 5C:
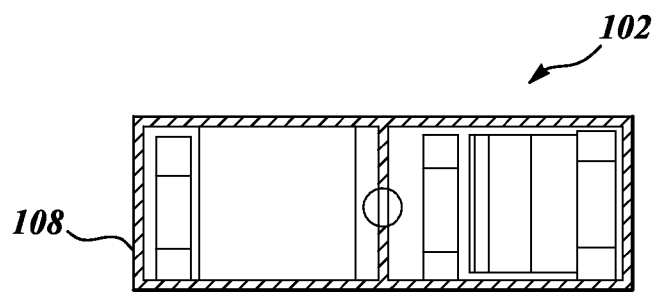
FIG. 5C is a bottom plan view of the drive unit of FIG. 5A, illustrating a port that provides fluid communication to a pendant from the housing of the drive unit.
Figure 5D:
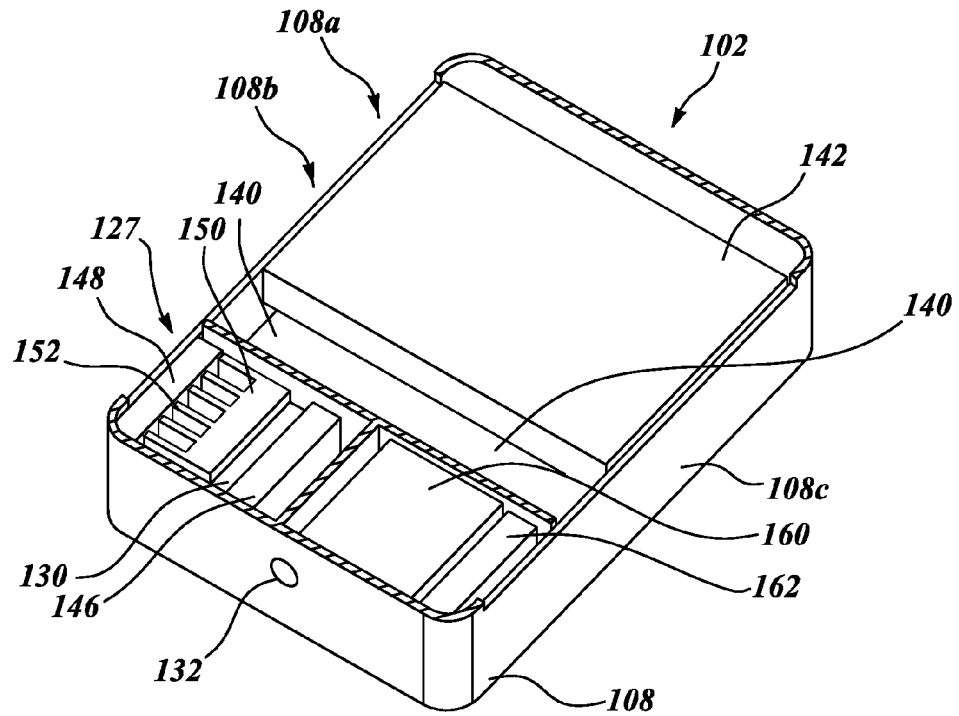
FIG. 5D is an isometric view of the drive unit of FIG. 5A, with the housing open to reveal an internal structure of the drive unit and various components of the drive unit housed in the housing.
Figure 5E:
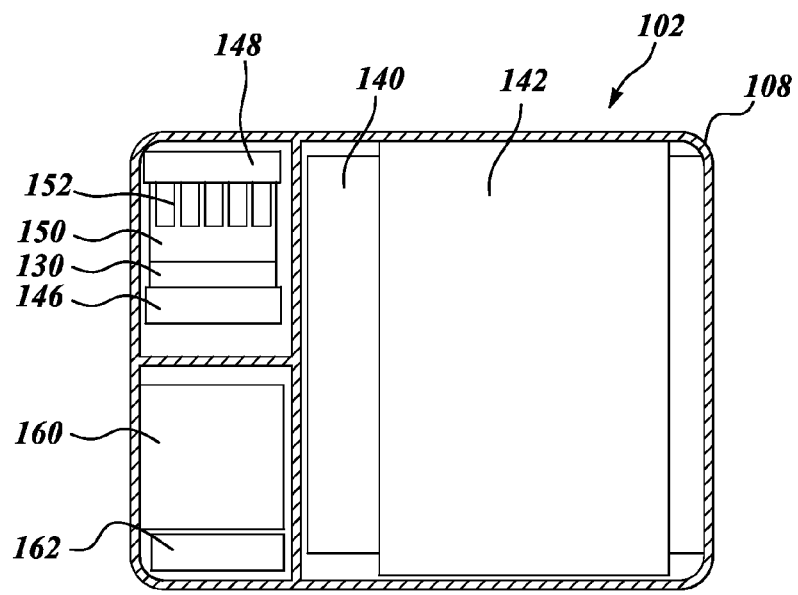
FIG. 5E is top plan view of the drive unit of FIG. 5D, with the housing open to reveal the internal structure of the drive unit and various components of the drive unit housed in the housing.

As best illustrated in FIGS. 5D and 5E, an interior of the housing 108 may be divided into separate compartments. For example, the interior of the housing 108 may be divided into an electronics compartment 108a, a scent generation or mixing compartment 108b, and a filter compartment 108c.

The electronics compartment 108a includes one or more circuit boards 140, for example one or more printed circuit boards (PCBs) which carry a control subsystem and various other electrical and electronic components. The electronics compartment 108a also houses one or more power sources. Power sources 142 may take any of a variety of forms, for example one or more chemical battery cells (e.g., lithium ion), super- or ultra-capacitor cells and/or fuel cells. The power sources may be rechargeable power sources, for instance secondary battery cells (e.g., nickel-cadmium, nickel-zinc, nickel metal hydride, lithium-ion)) or super- or ultra-capacitors. In such cases, the electronics may include conventional recharging circuitry. Alternatively, the power sources 142 may be consumable power sources such as primary batteries (e.g., zinc-carbon, alkaline), requiring eventual replacement.

The scent generation or mixing compartment 108a is where scents are generated or released from scent media 112 (FIG. 1) and/or mixed. In contrast to some conventional approaches, the drive unit 102 may mix the scents released from two or more different scent media 112 (FIG. 1), prior to delivery to a user. The scent generation or mixing compartment 108a houses the scent carrier receiver 130 and a number of scent release actuators positioned to cause selective release of scent from the scent media. The scent carrier receiver 130 may include a biasing member (e.g., resilient member, for instance Neoprene) to bias the scent media carrier 110 (FIG. 1) into firm contact with the scent release actuator(s). The scent media carriers may, for example, be oriented vertically to ensure separation between various pieces of scent media carried by the scent media carriers. The scent release actuator(s) may advantageously take the form of one or more Peltier devices 146. Peltier devices 146 advantageously allow both the active heating and active cooling of scent media 112 (FIG. 1), via the application of voltages of opposite polarities.

The scent generation or mixing compartment 102a may also house one or more fans 148. The fans 148 are operable to cause delivery of released scent outwardly of the drive unit 102, for example via the cable port 132. The fan(s) 148 may do so by creating a relatively high pressure upstream of the scent port 114a (FIG. 1). The fan(s) 148 should be miniature low power consumption fan(s). Thus, such fan(s) 148 may be denominated as scent delivery fan(s) for convenience of reference.

The scent generation or mixing compartment 102a may also house one or more heat sinks 150. The heat sinks 150 are preferably large thermal masses, able to quick sink or absorb heat. The heat sinks may take the form of a block of metal. Thermal paste may be employed between the surfaces of the heat sink and the Peltier devices. The scent generation or mixing compartment 102a may also house one or more heat dissipation structures 152. The heat dissipation structure(s) 152 are preferably thermally conductively coupled to the heat sink(s) 150. The heat dissipation structure(s) 152 will typically have a highly convoluted surface (e.g., fins, pin fins) to increase a surface area relative to a volume thereof. Such may facilitate transfer of heat via conduction and/or radiant heat transfer.

The filter compartment 108c holds filter media 160 that is effective at removing scent from air. The filter media 160 may be used to remove scent from air returned to the drive unit 108 from a scent port 114 (FIG. 1). Additionally or alternatively, filter media 160 may be used to remove scents from air drawn from the ambient environment to ensure that only the intended scent is delivered to the user.

The filter compartment 108c may also house one or more fans 162. The fans 162 are operable to draw air through the filter media 160. For example, the fans 162 may draw previously scented air toward the drive unit 108 from the scent port 114 (FIG. 1), for example via the cable port 132. The fan(s) 162 may do so by creating a relatively low pressure or partial vacuum downstream of the scent port 114 (FIG. 1). Also for example, the fans 162 may draw fresh air from the ambient environment, to be filtered prior to scenting. The fan(s) 162 should be miniature low power consumption fan(s). Thus, such fan(s) 162 may be denominated as scent withdrawal fan(s) for convenience of reference.

Suitable filter media 160 may, for example, include double-weave activated carbon fabric, although other filtering materials may be employed. Activated carbon fabric is particularly effective due to its micro porous surface and strong electrostatic forces within the fabric. Such filter media 160 is more efficient and has a higher absorption capacity than conventional granular carbon forms, when compared for equal volumes. Suitable double-weave activated carbon fabric may be that sold under the designation ZORFLEX ACC 100% activated carbon cloth.

For instance, eight layers of double-weave activated carbon fabric may be suitable. The filter media 160 should have a surface area that matches a diameter of the fan 162 used to circulate air or scented air through the filter media 160. The fan's 162 surface area may be a function of a diameter of the fan's blades rather than a frame of the fan 162. In some embodiments, the surface area may be approximately 162 mm$^2$. The total surface area of double-weave activated carbon fabric is approximately 2000 m$^2$/g, and the filter 160 may weigh approximately 2 grams, resulting in an effective surface area of approximately 4000 m$^2$. Testing of such filter media 160 indicated that such could be effectively used for 3.5 hours with no appreciable detection of scent by a human, and detection of only a slight hint of fragrance after 3.5 hours.

Figure 6A:
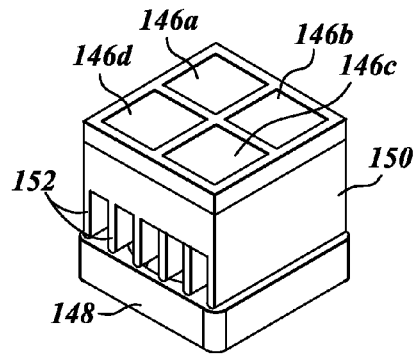
FIG. 6A is an isometric view of a scent actuator of the drive unit, according to one illustrated embodiment, which includes one or more Peltier devices, a heat sink, a convoluted thermal transfer structure, and one or more fans.
Figure 6B:
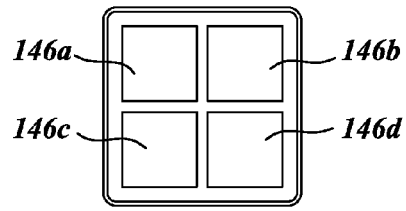
FIG. 6B is top plan view of the scent actuator of FIG. 6A.
Figure 6C:
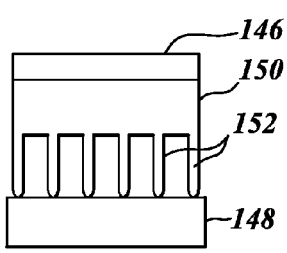
FIG. 6C is a side elevational view of the scent actuator of FIG. 6A.
Figure 6D:
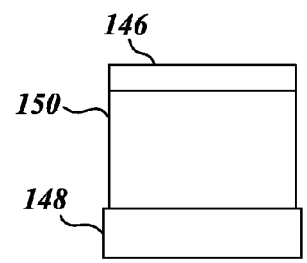
FIG. 6D is a front elevational view of the scent actuator of FIG. 6A.
Figure 6E:
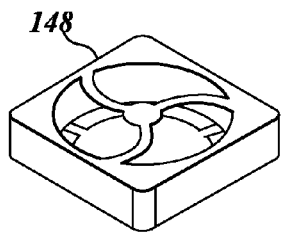
FIG. 6E is an isometric view of a fan of the scent actuator of FIG. 6A.
Figure 6F:
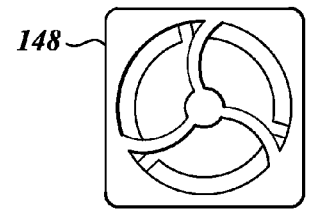
FIG. 6F is an isometric view of the fan of the scent actuator of FIG. 6A.
Figure 6G:
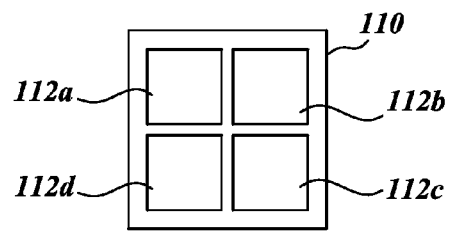
FIG. 6G is a top plan view of an exemplary scent media carrier showing a layout of scent media carried by the scent media carrier, according to one illustrated embodiment.

FIGS. 6A-6F show a scent actuation structure 600 of the drive unit 102, according to one illustrated embodiment. FIG. 6G shows a scent carrier 110 carrying four pieces or chips of scent media 112a-112d (collectively 112), according to one illustrated embodiment.

The scent actuation structure 600 may take a variety of forms which are operable to selectively cause release of scent from scent media 112 (FIG. 1, FIG. 6G). Suitable scent actuators of the scent actuator structure 600 typically employ heating, for example resistive heaters.

In the illustrated embodiment, the scent actuator structure 600 includes four discrete and separately operable scent actuators, advantageously in the form of Peltier devices 146a-146d (four shown, collectively 146). The Peltier devices 146 are operable to selectively actively heat or alternatively actively cool scent media 112. The Peltier devices 146 are spatially arranged to allow each Peltier device 146a-146d to be thermally conductively coupled with respect to a scent medium 112a-112d carried by a scent medium carrier 110 when the scent media carrier 110 is removably received in the scent media carrier receiver 132 (FIGS. 5D and 5E). Notably, a spatial layout of the Peltier devices 146 should match or otherwise be consistent with a spatial layout of scent media 112 on the scent media carriers 110. This allows control over release of scent from selected ones of the scent media 112 according to defined scent specifications or sets of scent delivery sequences. While illustrated as a two-dimensional 2×2 array, other spatial layout patterns may be employed. The spatial layout pattern may be an ordered array of one-dimension (i.e., linear array), square, rectangular or some other shape. The array may have any number of elements or units, in any desired arrangement (e.g., 1×4, 1×6, 2×3, 2×4, 2×5, 2×6, 3×2, 3×3, 4×4). Alternatively, the spatial layout may be non-ordered. It may also be desirable to have a density of Peltier devices 146 to scent media 112 higher than the one-to-one relationship illustrated. Such may allow more refined heating of any given piece or portion of scent media 112.

An optional conductive transfer layer (not shown) may thermally conductively couple the Peltier device(s) 146 to the scent media 112 or the removably received scent media carrier 110. The conductive transfer layer may, for example, take the form of a metal layer, for instance a layer of aluminum. Thus, the Peltier devices 146 can actively heat scent media 112 to selectively cause release of scent. For example, the Peltier devices 146 can heat a substrate material such as wax or other substance which contains or incorporates the scent in order to melt or partially melt such, thereby releasing scent. The Peltier devices 146 can actively cool scent media 112 to selectively stop or prevent the release of scent. For example, the Peltier devices 146 may cool wax or other substance to solidify such, thereby stopping the release of scent. The Peltier device 146 may even be turned OFF, to allow passive cooling of the scent media should that be desired. The operation of the Peltier device(s) 146 is controlled by application of a current of a first voltage to cause active heating, and a second voltage, opposite the first voltage, to cause active cooling.

Peltier devices 146 may be actuated (i.e., heating, cooling) individually. Alternatively or additionally, two or more of the Peltier devices 146 may be activated concurrently (i.e., temporally overlapping at least partially in time) or even simultaneously. While the total number and spatial layout of the Peltier devices 146 can be varied in any way desired, the number of Peltier devices 146 that can be concurrently operated will depend on available power. Thus, parameters of the power source and/or power supply may limit the operation of Peltier devices 146.

The scent actuation structure 600 may include or be thermally conductively coupled to a heat sink 150. Such facilitates transfer of heat from the Peltier device(s) 146 during cooling operation. The heat sink 150 may include or be thermally conductively coupled to a convoluted heat transfer surface 152, with a relatively large surface area (e.g., fins, pins) as compared to its volume to facilitate convective and/or radiant transfer of heat.

The scent actuation structure 600 may include or be in fluidly communicative association with one or more fans 148. Like the previously described fans, the fan(s) 148 should be miniature low power consuming fan. Operation of the fan(s) 148 circulates air about the heat sink and/or convoluted surface to facilitate convective heat transfer. Thus, such fan(s) 148 may be denominated as cooling fan(s) for convenience of reference. Vents 128 may provide circulation of air with the ambient environment to aid in cooling.

As best illustrated in FIG. 6G, the scent media carrier 110 may take any of a large variety of forms capable of carrying one, and preferably more, pieces or portions of scent media. The scent media carrier 110 may take the form of a card or cartridge, which is removable from the housing of the drive unit.

The scent media carrier 110 may take the form of a substrate which carriers one or more pieces or portions of scent media 112, for example wax infused with scent (e.g., essences). A copper foil or copper layer may provide thermal conduction.

The scent media carrier 110 may take other forms. For example, the scent media carrier 110 may take the form of a blister pack, which includes a carrier substrate and a membrane including a number of selectively rupturable blisters which retain scent media 112 therein between the blister and the carrier substrate. The scent media 112 may in the blister may, for example take a powder aerosolized type form, for instance having a size sufficiently small to create a powder aerosol convective dispersion once the respective blister is ruptured. In such embodiments, the scent actuator may not only include a mechanism for rupturing the blister(s), but may also include a mechanism to drive the powder aerosol into the air in the scent chamber. Such dispersal mechanism may take a variety of forms, for instance a nebulizer or ultrasonic transducer that produces vibrations at ultrasonic frequencies.

Alternatively, the scent media 112 may in the blister may, for example, take the form of a volatile substance. For instance, the scent media 112 may in the blister may take the form of a volatile liquid (e.g., alcohol based). In such embodiments, the scent actuator may only need to include a mechanism for rupturing the blister(s).

The scent media 112 may take any of a large variety of forms of material capable of holding and selectively releasing scent in response to some stimulus. Example forms include solid or semi-solid materials, for instance wax impregnated or incorporating scents, or fine powders. Example forms liquids, for instance volatile liquids.

The scent media 112 should also preferably be capable of stopping the release of scent in response to some stimulus, or removal of the stimulus which caused the release of scent. Stimuli may include application of heat, removal of heat, application of current, voltage, pressure, vibratory motion, or energy (e.g., ultrasonic vibration), application of electromagnetic energy (e.g., infrared light, ultraviolet light, microwaves), or even the selective rupturing, breaking, or puncturing of a membrane (e.g., self sealing membrane), blister, vial or other frangible structure.

The scent media 112 may take the form of paraffin wax with lipophillic or oil-based scents incorporated therein or underlying such. Paraffin wave has a relatively low melting point and a naturally neutral scent making such an excellent choice for the scent media. The scent media 112 may be made by melting paraffin wave and adding lipophillic scent in liquid form (e.g., essential oils). Typically, a saturation ratio of liquid scent to paraffin wave is 66-100 ml/Kg. The scent media 112 may be poured into thin sheets (e.g., 1-5 mm thick) and allowed to cool. The sheets may then be cut or otherwise divided into chips for placement on respective carriers. The sheets may be wrapped in a copper tape, either before or after being cut or otherwise divided. The copper tape may be placed in direct thermally conductive contact with the Peltier devices. Thermal paste may be used on contact surfaces between copper tape of the scent media 112 and the Peltier devices.

While illustrated as having four chips or patches of scent media 112 per scent media carrier 110, as noted herein the scent media carriers 110 may include a greater or lesser number of scent media chips or patches 112. Further, the scent media 112 may be laid out or arranged on the scent media carrier 110 in any desired layout or arrangement that approximately matches or is consistent with Peltier devices or other scent release actuators.

Figure 7A:
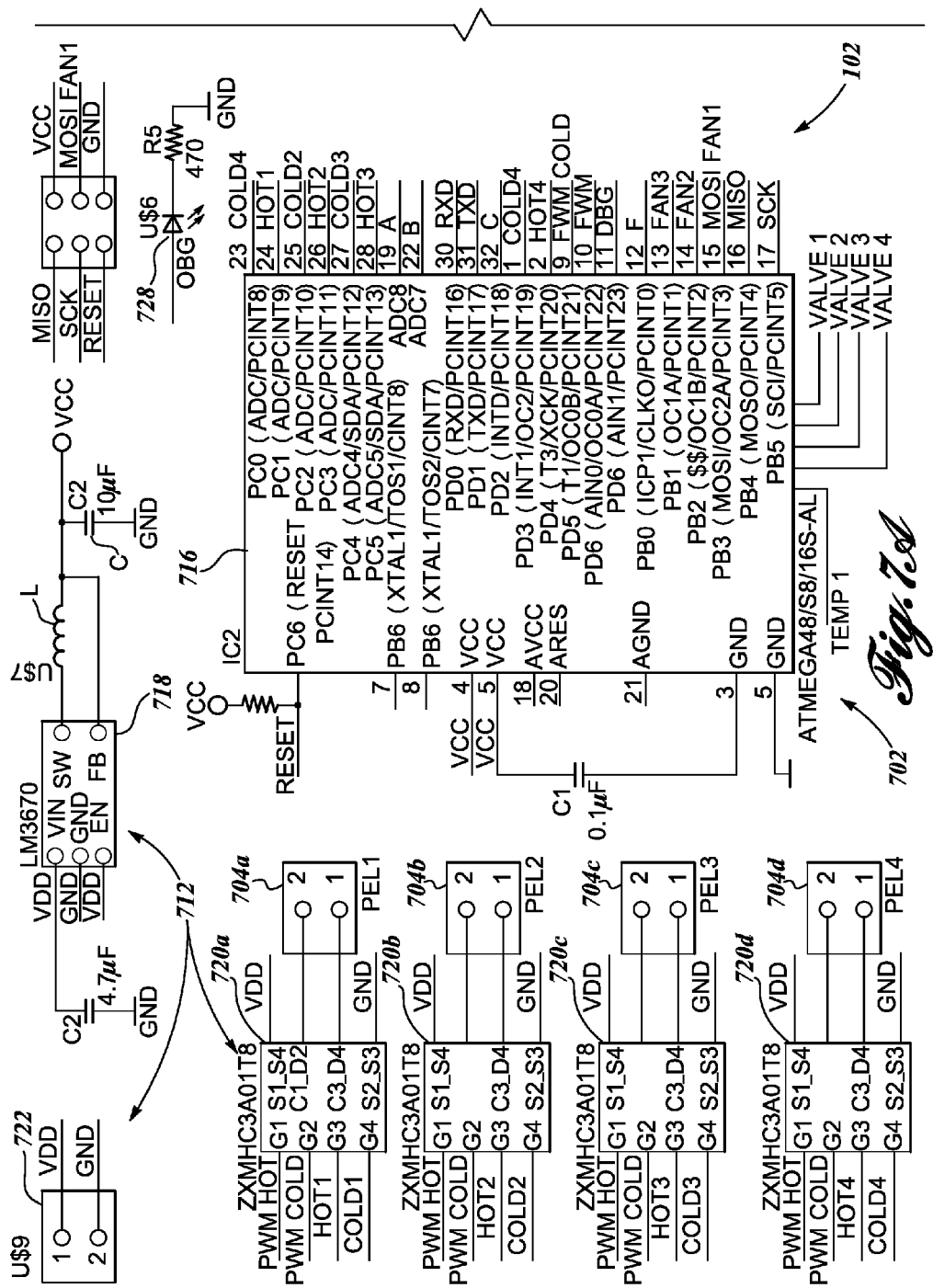
FIGS. 7A and 7B are an electrical schematic diagram of a control subsystem of the drive unit, including Peltier devices, fans, power supplies, and a communications subsystem.
Figure 7B:
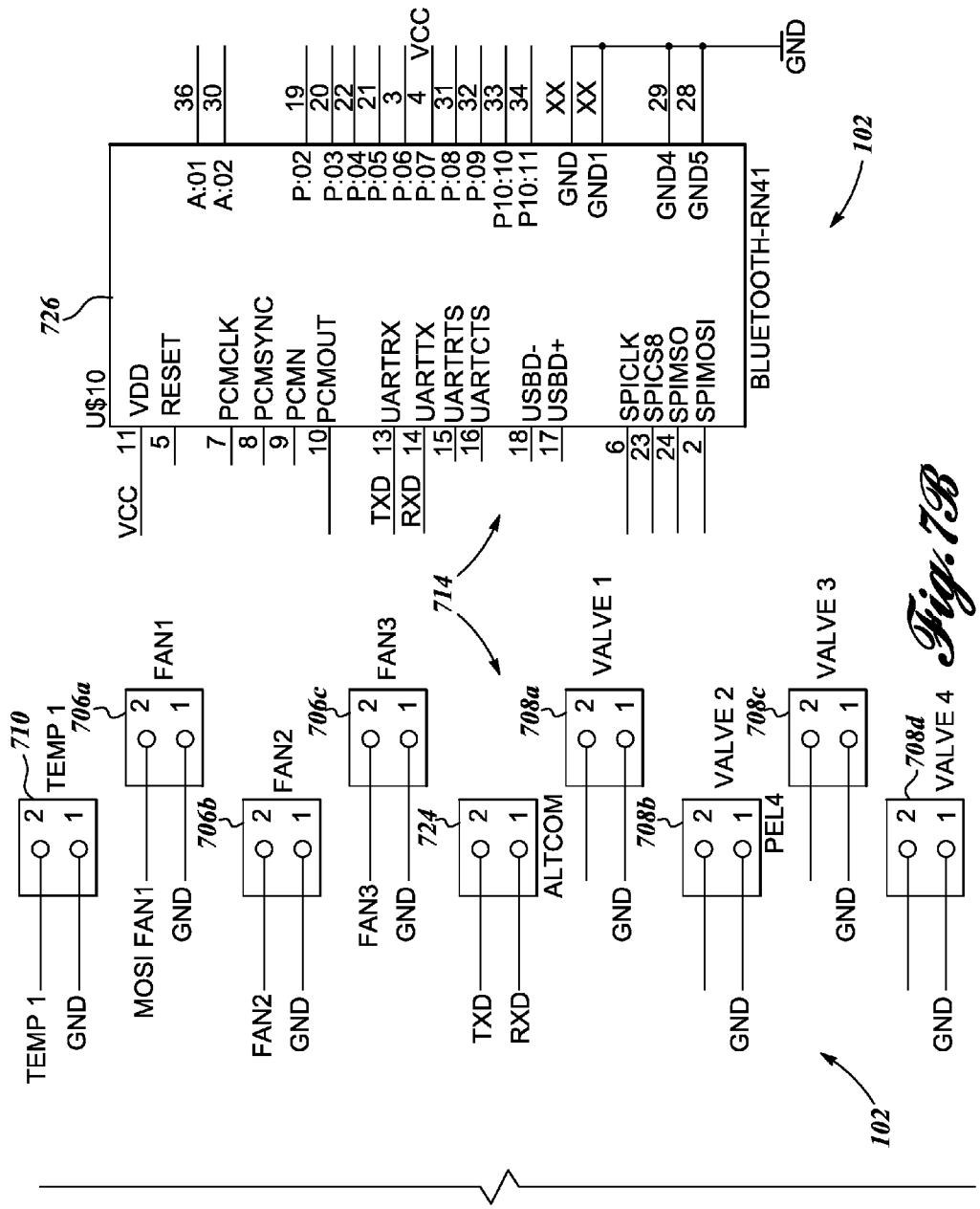

FIGS. 7A and 7B show various components of the drive unit 102, according to one illustrated embodiment.

The components may, for example, include a control subsystem 702, Peltier devices 704a-704d (four shown, collectively 704), fans 706a-706c (three shown, collectively 706), valves 708a-708d (four shown, collectively 704), sensors (e.g., temperature sensor 710), power supply subsystem 712, and communications subsystem 714. The drive unit 102 may include additional instances of the various components (e.g., 6, 8, 12 Peltier devices) or may include additional types of components (e.g., switches, acidometers, gyros). The drive unit 102 may omit some of the illustrated components. One or more of the components may be provided separately from the drive unit 102 or housing 108 in some implementations. For example, one or more valves 708 and/or sensors 710 or switches (not shown) may be provided in a pendant 104, where a pendant 104 is employed.

The control subsystem 702 may include a microcontroller 716 and discrete or integrated nontransitory storage media such as memory. A suitable microcontroller 702 may take the form of an 8-bit microcontroller with in-system programmable flash memory, such as the microcontroller commercially available from Atmel Corporation under designation ATMEGA48/88/168-AU. The microcontroller 716 executes a program stored in its memory, and sends signals to control the various other components, for instance the Peltier devices 704, fans 706, valves 708, etc. Control signals may, for instance be pulse width modulated (PWM) control signal, particularly where controlling an active power supply device (e.g., DC/DC power converters 718, 720a-720d discussed below). Otherwise, control signals may take on any of a large variety of forms. For instance, the microcontroller 716 may control fans 706 simply by completing a circuit that powers the respective fan 706. For instance, the microcontroller 716 may control valves 708 (discussed below with reference to FIG. 8A) simply by completing a circuit that powers the respective valve 708.

The power subsystem 712 may include one or more power sources 142 (FIGS. 5D, 5E) and one or more power supplies. The power supplies typically include DC-DC power converters, operable to step down voltage of a current to suitable levels for use with the other components. For example, a power supply 718 is coupled to the power source 142 and operable to step down a voltage from the power source 142 (e.g., secondary battery) to a level suitable for use with the microcontroller 716. The power supply 718 may be electrically coupled to a supply rail via an inductor L and capacitor C. A suitable power supply may include a step-down DC-DC power converter, such as the miniature DC-DC power converter suitable for ultra low voltage circuits commercially available from Texas Instruments under the designation LM3670. Additionally, the power subsystem may include one or more power supplies 720a-720d (four shown, collectively 720) coupled to supply electric power to the Peltier devices 704a-704d, at positive and negative voltages. For example, the power subsystem may include a respective power supply 720a-720d for each of the Peltier devices 704a-704d. Suitable power supplies 704 may take the form of MOSFET H-bridges, for example those commercially available from Zetex Semiconductor under the designation ZXMHC3A01T8.

The power subsystem 712 may include contacts, leads or nodes 722 (one set shown) to allow power to be supplied from an external source for charging the power source 142 (FIGS. 5D, 5E). Typically, the power will come via an external power supply (i.e., power brick), which may itself be electrically coupled to an outlet or main circuit (e.g., residential power). Alternatively, a power supply with rectifier and suitable DC-DC converter may be integrated into the drive unit, to control and/or condition electrical power to be suitable for charging the onboard power source 142 (FIGS. 5D, 5E).

The communications subsystem 716 may include one or more communications ports to provide communications to external devices or components. The communications ports may be wired and/or optical communications ports 724 (e.g., THUNDERBOLT®), or wireless communications port 726, and may be compliant with any of a large variety of related protocols (e.g., ETHERNET®, UNIVERSAL SERIAL BUS (USB®), FIREWIRE® 400, FIREWIRE® 800, THUNDERBOLT®, LIGHTNING®, WI-FI®, BLUETOOTH®, various IEEE 802.11 protocols, CDMA, GSM®, LTE®). The wireless communications port 726 may take the form of a BLUETOOTH® radio (i.e., wireless transmitter, receiver or transceiver). Suitable BLUETOOTH® radios may include small form factor, low power devices (RN41) commercially available from a variety of sources including Microchip and Roving Networks. The communications port (e.g., wired and/or optical 724, or wireless 726) may provide communications with at least one of a mobile communications device or a media player. Additionally or alternatively, a transmitter housed by at least one of the housing or a pendant may provide communications with a number of speakers (e.g., ear buds, headphones).

The drive unit 102 may optionally include a visual indicator 728 to indicate when the system 100 is operating or turned ON. Although illustrated as a single light emitting diode (LED), the visual indicator 726 may take any of a large variety of forms. The LED may be capable of emitting one, two or more distinct colors. The visual indicator 728 may also indicate other information or conditions, for instance the visual indicator 728 may flash in response to an occurrence of an error condition. A pattern of flashes (e.g., number of sequential flashes, color of flashes, number and color of sequential flashes) may be used to indicate which of a number of possible error conditions has occurred.

The control subsystem 702 is responsive to control the at least one Peltier device 704, fan(s) 706 and/or valve(s) 708 at least partially based on at least one of an orientation or a position of the second portion 126 of the pendant 104 (FIG. 1) relative to the first portion 124 of the pendant 104, or alternatively an orientation of the housing 108 (FIG. 1) of the drive unit 102.

The pendant 104 (FIGS. 2A, 2B, 3A, 3B), or alternatively the drive unit 102 (FIG. 1), may include one or more touch sensors (e.g., capacitive or inductive touch sensors) that sense human touch on at least a portion of the pendant, or the housing 108 of the drive unit 102. The control subsystem 702 may be responsive to control the at least one Peltier device 704, fan(s) 706 and/or valve(s) 708 at least partially based on sensed touches of the pendant or housing 108.

The pendant 104 (FIGS. 2A, 2B, 3A, 3B), or alternatively the drive unit 102 (FIG. 1), may include a motion sensor (e.g., MEMS accelerometer or gyroscope). The motion sensor may sense movement of at least a portion of the pendant 104, or alternatively the drive unit 102. The control subsystem 702 be responsive to control the at least one Peltier device 704, fan(s) 706 and/or valve(s) 708 at least partially based on sensed movement or acceleration of the pendant 104 (FIG. 1), or alternatively the drive unit 102 (FIG. 1).

The control subsystem 702 may be responsive to control the at least one Peltier device, fan(s) and/or valve(s) at least partially based on at least one of images or information displayed on a display (not called out) of a mobile communications device or the media content player 116 (FIG. 1) to which the drive unit 102 (FIG. 1) is communicatively coupled.

The control subsystem 702 may be responsive to control the at least one Peltier device 704, fan(s) 706 and/or valve(s) 708 at least partially based on user selections via user selectable icons or information displayed on a display (not called out) of a mobile communications device or the media content player 116 (FIG. 1) to which the drive unit 102 (FIG. 1) is communicatively coupled.

The control subsystem 702 may be responsive to control the at least one Peltier device 704, fan(s) 706 and/or valve(s) 708 at least partially based on images captured by an image sensor (not called out) of a mobile communications device or the media content player 116 (FIG. 1) to which the drive unit 102 (FIG. 1) is communicatively coupled.

Figure 8A:
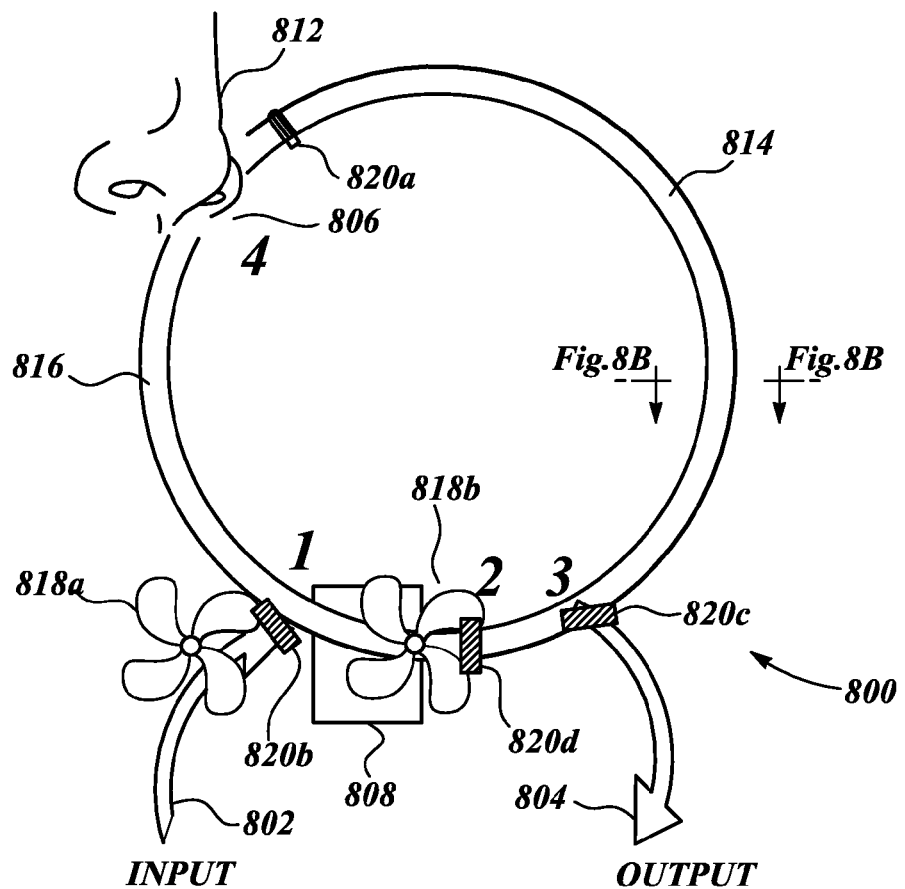
FIG. 8A is a schematic diagram of a configurable circulation system of personalized or multi-person embodiments of the system, according to one illustrated embodiment.

FIG. 8A shows a configurable circulation system 800 system according to one illustrated embodiment. Such may be suitable for use with pendant type systems (FIGS. 1, 2A, 2B, 3A, 3B, 4A, 4B), as well as for use with integral single piece systems (FIGS. 9A-9G), which can been used with various embodiments of the system 100, 900, 1002 operable to deliver scent or olfactory sensation.

The configurable circulation system 800 may be composed of a number of components such as conduits, valves, and/or air movers (e.g., fans, blowers). A particularly useful implementation is discussed below, however other implementations may be employed.

The configurable circulation system 800 may include one or more inlet vent(s) or port(s) 802, one or more outlet vent(s) or port 804 and one or more scent vent(s) or port(s) 806.

The inlet vent(s) or port(s) 802 provides fluid communication between an interior of the system 100 and an ambient environment. Such may be used to draw fresh air into the system, or to sample scents (e.g., coffee) from the ambient environment. The fluid communication via the inlet vent(s) or port(s) 802 may be selectively controllable, for example, via a first value or other structure. The inlet vent(s) or port(s) 802 may draw air from an ambient environment into the scent generation or mixing chamber 808. The air may, or may not, be filtered via filter media (not shown in FIG. 8A).

An outlet vent(s) or port(s) 804 provides fluid communication between an interior of the system 100 and an ambient environment. Such may be used to expel air from the system 100, for example after filtering. The fluid communication via the outlet vent(s) or port(s) 804 may be selectively controllable, for example via a second value or other structure. In some embodiments, the inlet and outlet vents or ports 802, 804 may be combined or implemented as a single port or ports which both draws and expels air. The outlet vent(s) or port(s) 804 may expel air to the ambient environment. The air is preferably filtered via the filter media (not shown in FIG. 8A) in the filter chamber (not shown in FIG. 8A) prior to being expelled to prevent or minimize the unintentional delivery of scent to the ambient environment. The scent vent(s) or port(s) 806 provides scent (e.g., intentionally scented air) to the user, preferably proximate the user's nose 812.

The configurable circulation system 800 may include a scent delivery conduit 814 that provides fluid communication between the scent generation or mixing chamber 808 and the scent vent(s) or port(s) 806 that in use releases scent to a user from the scent delivery conduit 814. As previously illustrated, the scent port(s) 806 may be located in a pendant 104*a* (FIG. 1). In such an implementation, the scent delivery conduit 814 may be in or part of a cable 106 (FIG. 1) that runs from the housing 108 (FIG. 1) of the drive unit 102 (FIG. 1) to the scent vent(s) or port(s) 806 in the pendant 104*a*. Alternatively, a scent vent(s) or port(s) 806 may be located in the housing 108 of the drive unit 102 (FIGS. 5A-5E). As previously noted, one or more fan(s) 818*a*-818*c* may drive the scented air along the scent delivery conduit 814, for example by creating a relatively high pressure upstream of the scent vent(s) or port(s) 806.

The configurable circulation system 800 may include a scent return or withdrawal conduit 816 that provides fluid communication between the scent vent(s) or port(s) 806 and the filter chamber (not shown in FIG. 8A) of the drive unit 102. As previously illustrated, the scent vent(s) or port(s) 806 may be located in a pendant 102*a* (FIG. 1). In such an implementation, the scent return or withdrawal conduit 816 may be in or part of a cable 106 (FIG. 1) that runs from the housing 108 of the drive unit 102 to the scent vent(s) or port(s) 114 in the pendant 104*a* (FIG. 1). Alternatively, a scent vent(s) or port(s) 806 may be located in the housing 108*a* of the drive unit 102 (FIGS. 5A-5E). As previously noted, one or more fan(s) 818*a*-818*c* may draw the scented air along the scent return or withdrawal conduit 816, for example by creating a relatively low pressure or partial vacuum downstream of the scent vent(s) or port(s) 806.

The scent delivery and the scent return or withdrawal conduits 814, 816 may take a variety of forms. The scent delivery and the scent return or withdrawal conduits 814, 816 may each be a piece of tubing. The scent delivery and the scent return or withdrawal conduits 814, 816 preferably have relative small outer diameters, and are flexible or compliant so as to be easily worn by a user. Relatively small diameters mean that the inner diameters will also be relatively small. It may also be preferable to have relatively turbulent flow within the conduits, as opposed to laminar flow. While various materials are suitable, materials capable of producing turbulent flow at the speeds, pressures, temperatures and dimensions involved are preferred. Particularly suitable conduits include ones formed of neoprene, having an outer diameter of approximately 3.0 mm and an inner diameter of approximately 1.5 mm. The neoprene tubing is preferably stretched lengthwise prior to use. Stretching may advantageously increase surface roughness of the inner diameter, facilitating development of turbulent flow therein. Stretching may also slightly decrease wall thickness of the tubing while also increasing pliability. Other possibly suitable tubing includes neoprene having an outer diameter of approximately 4.0 mm and an inner diameter of approximately 2.5 mm. Other possible choices include pure silicone, latex, and PVC/vinyl, although these appear less suitable that neoprene.

Figure 8B:
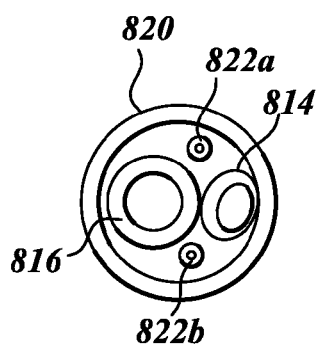
FIG. 8B is a cross-sectional view of a cable of the configurable circulation system of FIG. 8A, including a scent delivery conduit, a scent return or withdrawal conduit, and a number of wires, according to one illustrated embodiment.

As best illustrated in FIG. 8B, the conduits 814, 816 are housed by a cable 820. The cable 820 may additionally include a number of wires or optical fibers 822*a*, 822*b* (collectively 822) to pass signals to a number of speakers. For example, the wires or optical fibers 822 may pass audio signals from audio source, for instance a mobile communications device or the media player 116, through the drive unit 102, 102*a* to the speakers (e.g., ear buds, headphones) 122 (FIG. 1).

While illustrated as tubular conduits, the scent delivery conduit 814 and/or scent return or withdrawal conduit 816 may be formed by portions of the housing 108, 108*a* or other structure which forms a defined path or enclosed path. Such portions may preferably have a rough inner surface to promote turbulent flow.

Returning to FIG. 8A, the configurable circulation system 800 may include a scent port valve 820*a*. The scent port valve 820*a* is selectively operable, for example via signals from a microcontroller to an actuator, to control passage of scents via the scent port(s) 806. The scent port valve 802*a* may take the form of a pinch valve mechanism and an actuator (e.g., electric motor, solenoid) coupled to movingly drive the pinch valve mechanism.

The configurable circulation system 800 may include an inlet valve 820*b* positioned and selectively operable to control passage of scent into the scent mixing chamber from the ambient environment. The inlet valve 820*b* may be positioned in the housing 108 of the drive unit 102. The inlet valve 820*b* is selectively operable, for example via signals from a microcontroller to an actuator, to control passage of ambient air into the scent generation or mixing chamber. The inlet valve 820*b* may take the form of a pinch valve mechanism and an actuator (e.g., electric motor, solenoid) coupled to movingly drive the pinch valve mechanism.

The configurable circulation system 800 may include an outlet valve 820*c* positioned and selectively operable to control passage of scent to or through the filter chamber from the configurable fluidly communicative conduit path. The outlet valve 820*c* may be positioned in the housing 108 of the drive unit 102. The outlet valve 820c is selectively operable, for example via signals from a microcontroller to an actuator, to control passage of scents to or from the filter chamber. The outlet valve 820c may take the form of a pinch valve mechanism and an actuator (e.g., electric motor, solenoid) coupled to movingly drive the pinch valve mechanism.

The configurable circulation system 800 may include an intermediary valve 820d positioned and selectively operable to regulate passage of scent from the scent return or withdrawal conduit 816 to the scent delivery conduit 814 of the fluidly communicative conduit path, essentially recirculating or reusing previously scented air and creating a somewhat closed loop scent circulation or recirculation loop or system. The intermediary valve 820d may be positioned in the housing 108 of the drive unit 102. The intermediary valve 820d is selectively operable, for example via signals from a microcontroller to an actuator, to control or regulate passage of scents to or from the filter chamber. The intermediary valve 820d may take the form of a pinch valve mechanism and an actuator (e.g., electric motor, solenoid) coupled to movingly drive the pinch valve mechanism.

One or more fans 818a, 818b (two shown in FIG. 8A) may provide or cause the circulation through the configurable fluid circulation path. Fan(s) 818 may be selectively operable and/or may be operated at selected speeds to achieved directed flows. In some instances, one or more fans(s) may be operated to establish a relatively low pressure of vacuum in part of the configurable fluid circulation path, drawing air or scent along a desired portion of the configurable fluid circulation path.

The embodiments of FIGS. 8A and 8B should not be considered limiting.

FIGS. 9A-9G show a system 900 operable to delivery scent or olfactory sensation, according to one illustrated embodiment. In particular, FIGS. 9A-9G show the system 900 in a personalized form, for delivering scent or olfactory sensation to individual users (i.e., scent consumers).

In contrast to the system 100 (FIG. 1), the system 900 illustrated in FIGS. 9A-9G locates one or more scent ports or vents 904 integral to the drive unit 902. Such eliminates the need for a pendant 104a (FIG. 1).

Figure 9A:
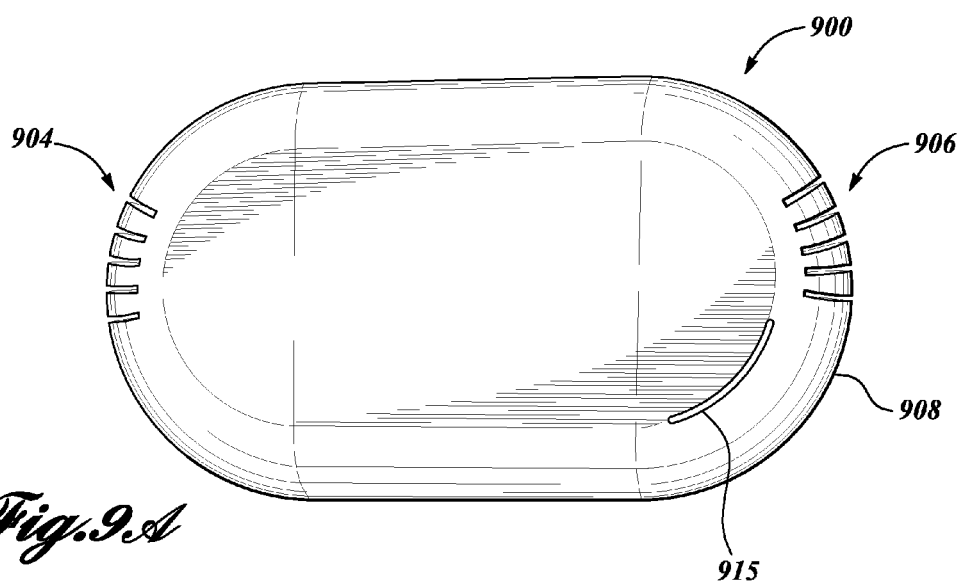
FIG. 9A is a top plan view of a system operable to deliver scent or olfactory sensation in a personalized form that includes a drive unit with integral scent port(s), according to one illustrated embodiment.
Figure 9B:
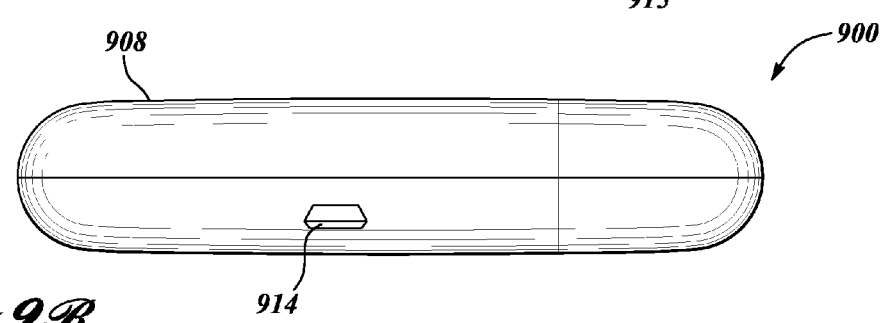
FIG. 9B is a side elevational view of the system of FIG. 9A, according to one illustrated embodiment.
Figure 9C:
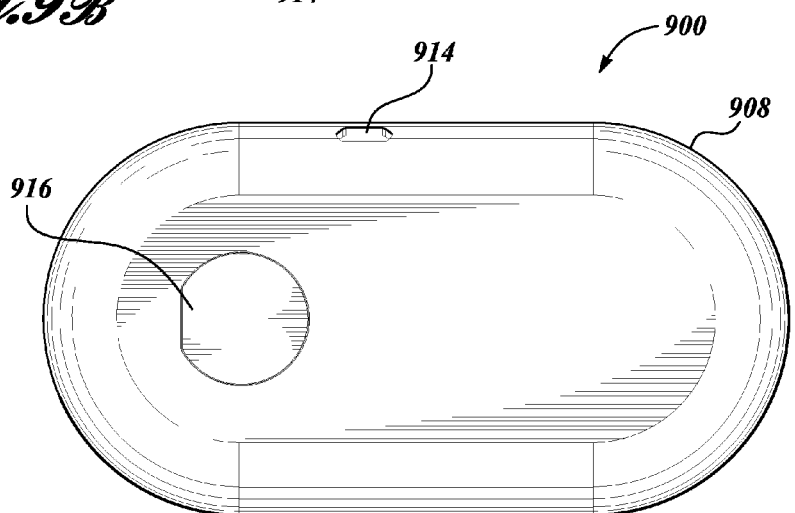
FIG. 9C is a bottom plan view of the system of FIG. 9A, illustrating a cover, according to one illustrated embodiment.
Figure 9D:
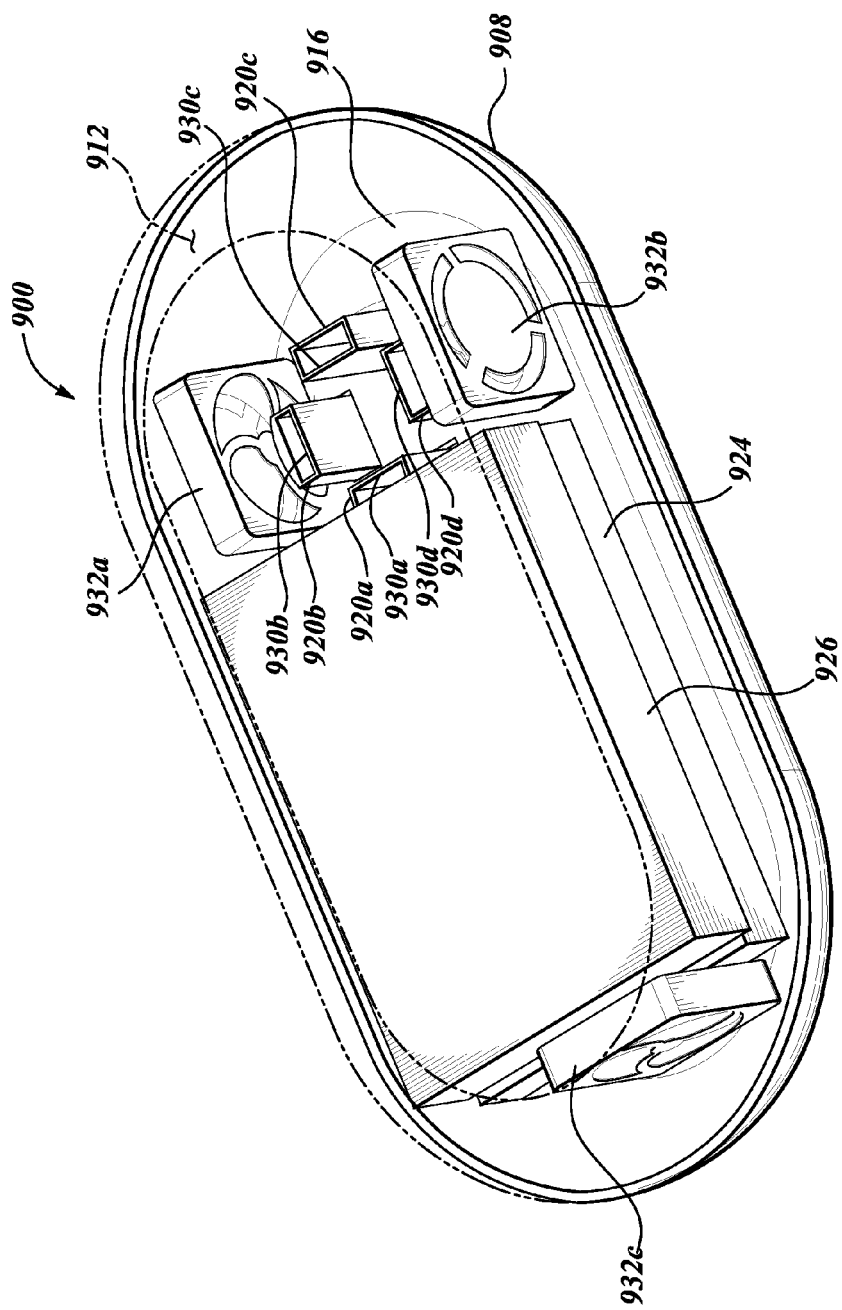
FIG. 9D is a top, right, front isometric view of the system of FIG. 9A with the housing shown as transparent to illustrate components housed in the housing, according to one illustrated embodiment.

As best illustrated in FIGS. 9A-9C, the system 900 includes an integral housing 908 which houses the various components of the system 900. The housing 908 may be formed of a variety of materials, for example metals (e.g., aluminum) or plastics (e.g., ABS plastics, polycarbonate plastics). The type of material or process employed to form the housing 908 from the material should not be considered limiting. The housing 908 preferably has a handheld form factor.

The housing 908 includes the scent vent(s) or port(s) 904, as well as a number of vents or ports 906. The scent vent(s) or port(s) 904 and vents or ports 906 provide fluid communication between an interior 912 (FIGS. 9D-9F) of the housing 908 and an ambient exterior environment. The vents or ports 906 may serve as inlets or intake vent(s) or port(s), to draw ambient air and scents into the housing. Additionally or alternative, the vent(s) or port(s) 906 may serve as outlet vents or ports to expel air into the ambient environment. Thus, vent(s) or port(s) 906 may be denominated as ambient vents or ports 906.

As best seen in FIGS. 9B, 9C, 9F and 9G, the housing 908 may also optionally include a communications port or interface 914. The communications port or interface 914 may take any of a large variety forms, compatible with various communications protocols. For example, the communications port or interface 914 may take the form of a receptacle or socket to receive a male USB plug. Such may provide communicative coupling to a mobile communications device (e.g., smart phone) or media content player (e.g., MP3 player, IPOD®, tablet computer, netbook computer, laptop computer) 116 (FIG. 1). Alternatively or additionally, the system 900 may employ a wireless interface (e.g., radio).

The housing 908 may be one or more user actuatable controls accessible from an exterior of the housing 908. As best seen in FIG. 9A, the user actuatable controls may include a simple switch 915 which allows the system to be turned ON and OFF and/or switched between various operating modes (e.g., active scent generation mode, passive scent sampling mode, and/or between various flow path configurations such as record/sample, hold, and release flow path configurations, discussed in detail with reference to FIGS. 10A-10E).

Figure 9F:
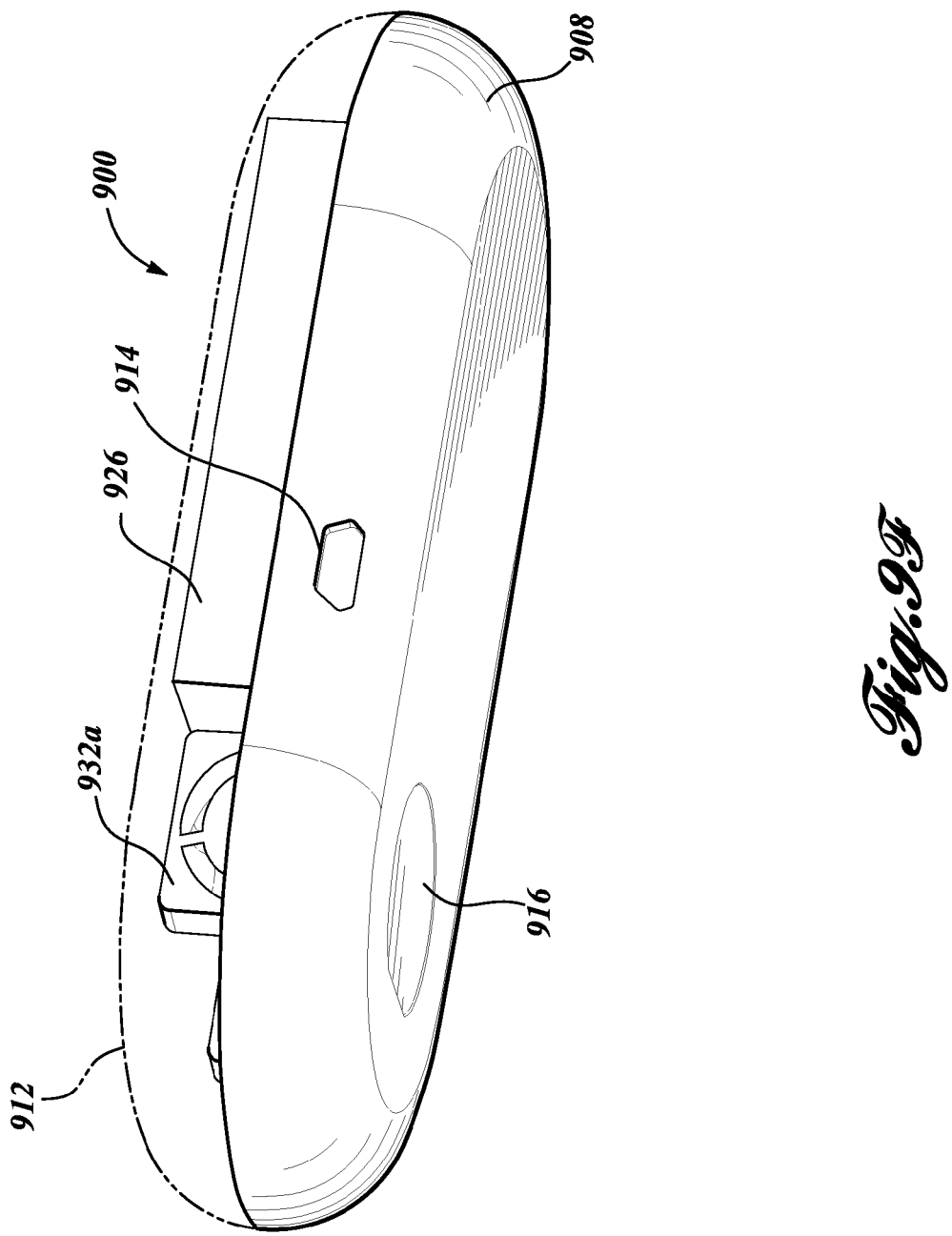
FIG. 9F is a bottom, left, rear isometric view of the system of FIG. 9A with the housing shown as transparent to illustrate components housed in the housing, according to one illustrated embodiment.
Figure 9G:
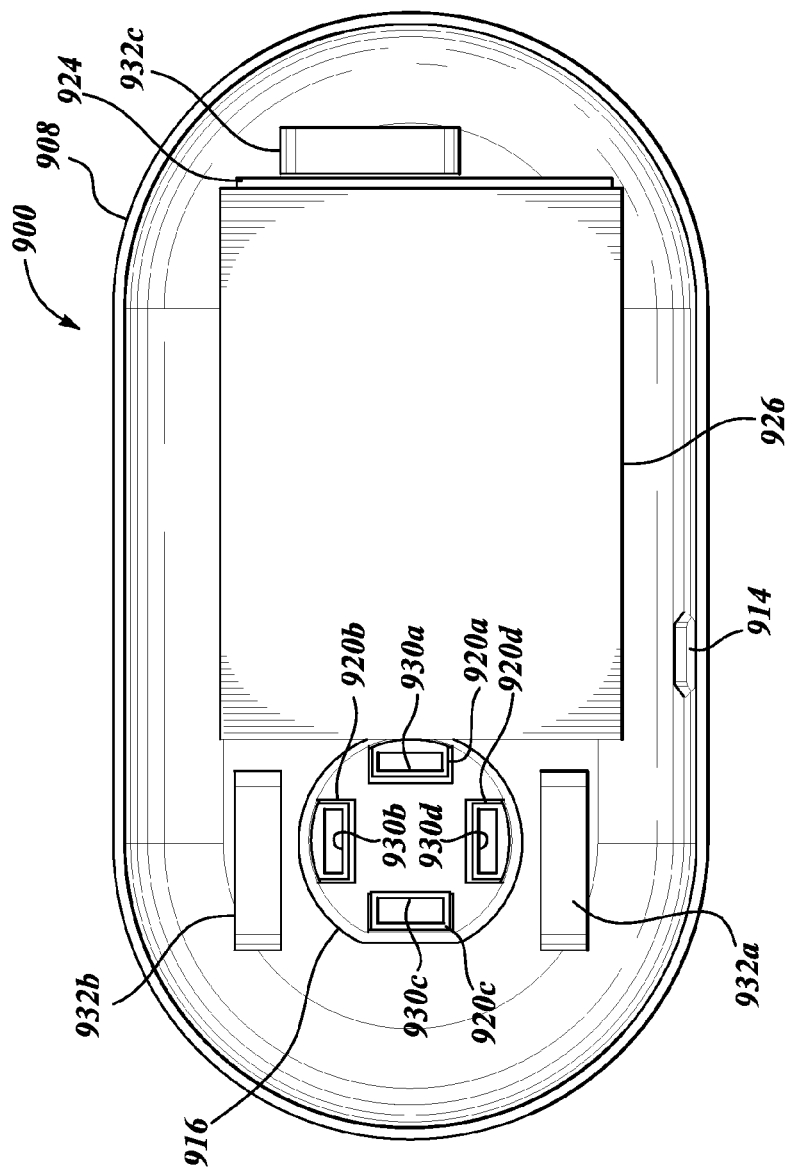
FIG. 9G is a bottom plan view of the system of FIG. 9A with the housing shown as transparent to illustrate components housed in the housing, according to one illustrated embodiment.

A portion of the housing 908 may be moveable to provide access to at least a portion of the interior 912 thereof. For example, as best illustrated in FIGS. 9C, 9F, the housing 908 may have a cover 916 mounted (e.g., removably, releasably, pivotally, slideably) to a main body portion of the housing 908. The cover 916 may provide selective access for inserting and removing scent carriers 110 (FIGS. 1, 6G). Alternatively, the housing 908 may include a slot sized and dimensioned to removably receive scent carriers 110, similar to that shown for the embodiment of FIG. 1.

As best illustrated in FIGS. 9D-9G, the housing 908 may house various components, many of the components similar or even identical to the previously described components. Some of these components are discussed below.

The housing 908 may house one or more scent carrier receivers 920a-920d (four shown, collectively 920). The scent carrier receiver(s) 920 may take the form of a frame of similar alignment structure which positions and/or orients a received scent media carrier 110 (FIGS. 1, 6G) with respect to one or more scent actuators (e.g., Peltier devices discussed below). The scent carrier receiver(s) 920 may be mounted on the cover 916, as illustrated. The cover 916 may be releasably coupled to the housing 908 with the scent carrier receivers 920 received or positioned within the interior 912 of the housing 908. The cover 916 may be releasably coupled to the housing 908, for example, via a detent mechanism such a tab or tongue which engages a lip or flange. The cover is selectively removed from the housing, providing access to the scent carrier receiver(s) 920 for loading of scent media carriers 110. The cover 916 may have a non-symmetric profile or other structure to ensure that the cover, and hence the scent carrier receiver(s) 920 is/are oriented in a defined fashion in the housing 908.

The housing 908 may house one or more circuit boards 924 (FIGS. 9D, 9E, 9G), for example one or more printed circuit boards (PCBs) which carry a control subsystem and various other electrical and electronic components. The housing 908 also houses one or more power sources 926. Power sources 926 may take any of a variety of forms, for example one or more chemical battery cells (e.g., lithium ion), super- or ultra-capacitor cells and/or fuel cells. The power sources 926 may be rechargeable power sources, for instance secondary battery cells (e.g., nickel-cadmium, nickel-zinc, nickel metal hydride, lithium-ion) or super- or ultra-capacitors. In such cases, the electronics may include conventional recharging circuitry. Alternatively, the power sources 926 may be consumable power sources such as primary batteries (e.g., zinc-carbon, alkaline), requiring eventual replacement. The electronics may, for example, be similar or even identical to that illustrated in FIGS. 7A and 7B.

A number of scent release actuators 930a-930d (four shown, collectively 930) are thermally coupled to respective ones of the scent carrier receiver(s) 920 to cause selective release of scent from the scent media 112 (FIGS. 1, 6G). The scent release actuator(s) 930 may advantageously take the form of one or more Peltier devices. Peltier devices advantageously allow both the active heating and active cooling of scent media 112 (FIGS. 1, 6G), via the application of voltages of opposite polarities. The scent carrier receiver(s) 920 may be sized and dimensioned to retain the scent media carrier(s) 110 into firm contact with the scent release actuator(s) 930. Additionally or alternatively, the scent carrier receiver(s) 920 may include a biasing member (e.g., resilient member) to bias the scent media carrier 110 (FIG. 1) into firm contact with the scent release actuator(s) 930.

The housing 908 may also house one or more fans 932a-932c (three shown, collective 932). The fans 932 exhaust heat generated by the electronics and Peltier devices, draw ambient air into the housing 908 via vents or ports 906, and expel scent air from the housing 908 via the scent vent(s) or port(s) 904. The fan(s) 932 should be miniature low power consumption fan(s).

The scent generation or mixing compartment 102a may also house one or more heat sinks (not shown). The heat sinks are preferably large thermal masses, able to quick sink or absorb heat. The heat sinks may take the form of a block of metal. The scent generation or mixing compartment 102a may also house one or more heat dissipation structures (not shown). The heat dissipation structure(s) are preferably thermally conductively coupled to the heat sink(s). The heat dissipation structure(s) will typically have a highly convoluted surface (e.g., fins, pin fins) to increase a surface area relative to a volume thereof. Such may facilitate transfer of heat via conduction and/or radiant heat transfer.

While not illustrated in FIGS. 9A-9G, the system 900 may optionally include filter media that is effective at removing scent from air. The filter media may be used to remove scent from air drawn from the ambient environment to ensure that only the intended scent is delivered to the user.

FIG. 10A shows the system 900 of FIGS. 9A-9G in an OFF state. Notably, in the OFF state, there is no circulation or flow 1002a between the scent vent(s) or port(s) 904 and the ambient vent(s) or port(s) 906. Hence there is no circulation or flow pattern in the housing 908.

FIG. 10B shows the system 900 of FIGS. 9A-9G in an ON state in an active scent generation mode (i.e., scent actuators active). In contrast to the OFF state, in the ON state the flow configuration includes a circulation or flow pattern 1002b in the housing 908. In particular, there is a direct circulation or flow between the ambient vent(s) or port(s) 906 and the scent vent(s) or port(s) 904. In operation, ambient air is drawn into the housing 908 via the ambient scent vent(s) or port(s) 904, passed by the scent media carrier receivers where the scent media 112 (FIGS. 1, 6G) is actively heated to release scent. The scented air is then expelled via the scent vent(s) or port(s) 904.

FIG. 10C shows the system 900 of FIGS. 9A-9G in an ON state in a passive ambient sampling mode (i.e., scent actuators not active). In contrast to the active generation mode, the passive mode is used to sample ambient air without active scent generation. In particular, FIG. 10C shows a record or sampling configuration used to capture samples of air or scents from the ambient environment, for example coffee, freshly baked cookies, or a flower. In the passive mode and record configuration, ambient air is drawn into the housing via the ambient vent(s) or port(s) 906 by one or more fans 932 (FIGS. 9A-9G). The scent vent(s) or port(s) 904 is/are closed, hence the sampled ambient air or scent circulates or flows 1002c, cycling around or through the housing 908 in a loop. As illustrated by the outward flow from the ambient vent(s) or port(s) 906, the ambient vent(s) or port(s) 906 may allow venting of air from the housing as the ambient air or scent is drawn into the housing.

FIG. 10D shows the system 900 of FIGS. 9A-9G in an ON state in the passive ambient sampling mode (i.e., scent actuators not active). In particular, FIG. 10D shows a conserve configuration. In the conserve configuration no new ambient air flows into the housing 908. The ambient vent(s) or port(s) 906 and the scent vent(s) or port(s) 904 are closed, the ambient air or scent previously captured in the record configuration circulates or flows 1002d around the interior of the housing 908. Such retains ambient air and/or scent previously captured from the ambient environment. Such may, for example, provide an opportunity for a user to raise the system 900 toward the user's nose to hopefully enjoy the scent. The hold configuration may be automatically entered a set or defined time after the start of the record configuration. Alternatively, the hold configuration may be entered manually, in response to user input.

FIG. 10E shows the system 900 of FIGS. 9A-9G in an ON state in the passive ambient sampling mode (i.e., scent actuators not active). In particular, FIG. 10E shows a release configuration. In the release configuration, the air or scent previously captured and held is released via the scent vent(s) or port(s) 904. In order to prolong the experience, such is preferably performed without drawing new ambient air into the housing 908, with the previously captured scent continuing to circulate, flow or cycle 1002e through the interior of the housing 908 for release via the scent vent(s) or port(s) 904. The release configuration may be automatically entered a set or defined time after the start of the hold configuration. Alternatively, the release configuration may be entered manually, in response to user input.

Each of the above described states, modes and configurations may be entered by supplying control signals to various components, such as scent actuators 930, fans 932, valves, etc. For example, an inlet valve or damper 1004a may be activated via one or more actuators (e.g., electric motor, solenoid) to selectively OPEN and CLOSE the scent vent(s) or port(s) 904. The inlet valve or damper 1004a is illustrated in a CLOSED position or state in FIGS. 10A, 10D and 10E. The inlet valve or damper 1004a is illustrated in an OPEN position or state in FIGS. 10B and 10C.

Also for example, an outlet valve or damper 1004b may be activated via one or more actuators (e.g., electric motor, solenoid) to selectively OPEN and CLOSE ambient vent(s) or port(s) 906. The outlet valve or damper 1004b is illustrated in a CLOSED position or state in FIGS. 10A, 10C and 10D. The outlet valve or damper 1004b is illustrated in an OPEN position or state in FIGS. 10B and 10E.

Also for example, an intermediary valve or damper 1004c (also called reflow, recycle or recirculation valve or damper) may be activated via one or more actuators (e.g., electric motor, solenoid) to selectively OPEN and CLOSE a recirculation path. The intermediate valve or damper 1004c is illustrated in an OPEN position or state in at least FIGS. 10C, 10D and 10E.

Operational Environment

Figure 11:
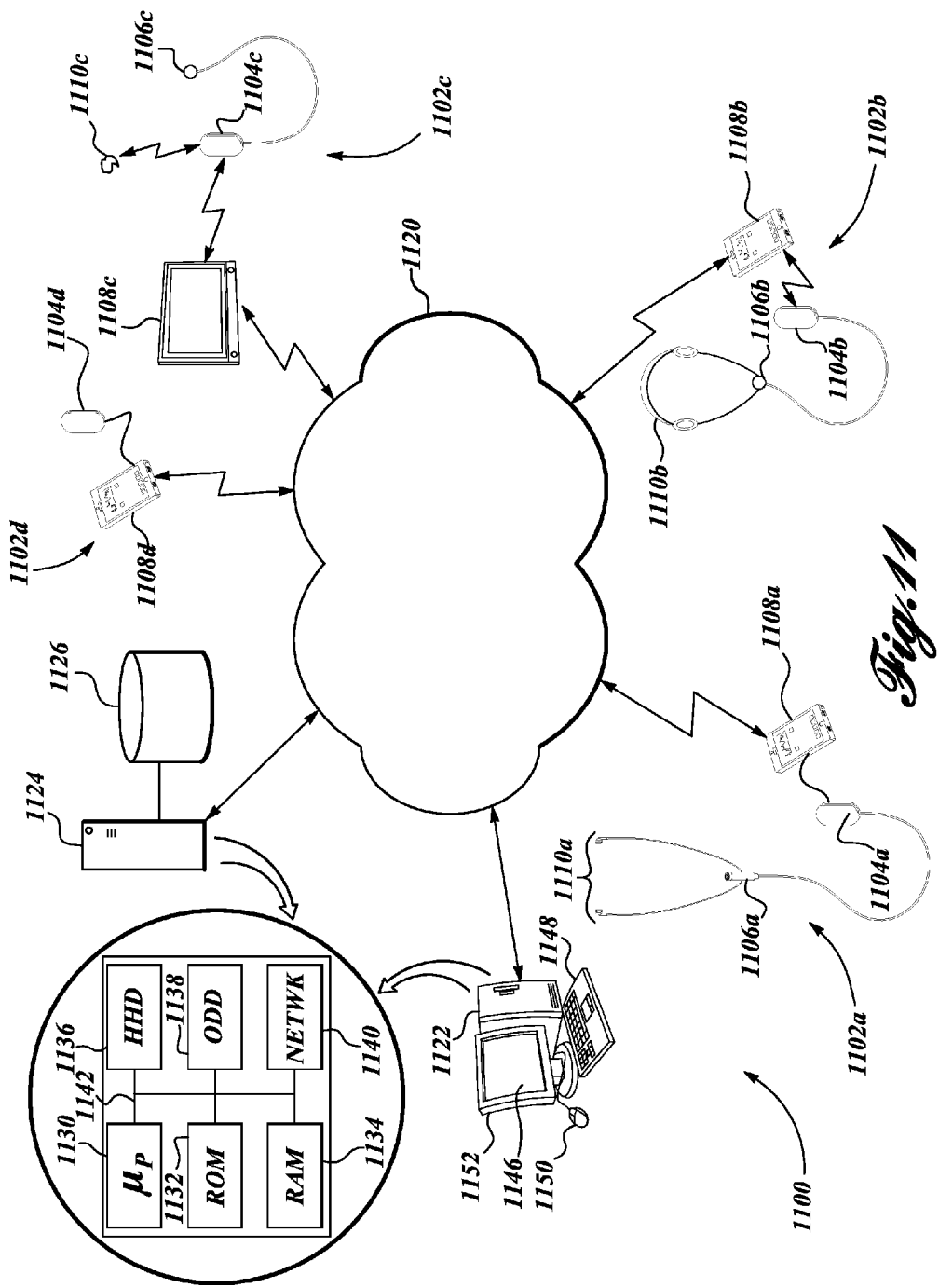
FIG. 11 is a schematic diagram of an operational environment in which a plurality of the systems for delivering scent are communicatively coupled to respective mobile communications devices or media content players, the operational environment including user computer systems and a sever computer system that functions as a Web portal for creating, editing, storing, and delivering scent specifications or sets of scent delivery sequences, with or without media content, according to one illustrated embodiment.

FIG. 11 shows an operational environment 1100 in which one or more of the systems 1102a-1102d (four shown, collectively 1102) operate, according to one illustrated embodiment.

In particular, FIG. 11 shows a plurality of systems 1102, each system 1002 including a drive unit 1104a-1104d (four shown, collectively 1104), and optionally a respective pendant 1106a-1106c (three shown, collectively 1106).

The components of drive units 1104 are communicatively coupled to respective mobile or wireless communications devices or media players 1108a-1108d (four shown, collectively 1108).

For instance, a first system 1102a is communicatively physically coupled by a cable (not called out in FIG. 11) to a respective mobile or wireless mobile communications device such as a smart phone or a feature phone 1108a. The components of the first drive unit 1104a are physically coupled to the respective pendant 1106a via a cable (not called out in FIG. 11). Further cable(s) (not called out in FIG. 11) physically couple the components of the drive unit 1103a to a number of speakers, illustrated as ear buds 1110a, via the pendant 1106a.

Also for instance, a second system 1102b is communicatively wirelessly coupled to a respective wireless or mobile communications device such as a smart phone or a feature phone 1108b. The components of the second drive unit 1104b are physically coupled to the respective pendant 1106b via a cable (not called out in FIG. 11). Further cable(s) (not called out in FIG. 11) physically couple the components of the drive unit 1104b to a number of speakers, illustrated as over ear headphones 1110b, via the pendant 1106b.

Also for instance, a third system 1102c is communicatively wirelessly coupled to a respective mobile or wireless mobile communications device such as a table computer 1108c. The components of the third drive unit 1104c are physically coupled to the respective pendant 1106c via a cable (not called out in FIG. 11). The components of the third drive unit 1104c are wireless communicatively directly coupled to a speaker, illustrated as a BLUETOOTH® headset 1110c intended to be worn on, in, or over an ear.

Also for instance, a fourth system 1102d is communicatively wirelessly coupled to a respective mobile or wireless mobile communications device such as a Smartphone 1108d. The fourth system may omit any pendant or cables, being a fully integrated device, similar to that illustrated in FIGS. 9A-9F, which may be employed with or without speakers.

The various wireless or mobile communications devices or media content players 1108 are communicatively coupled via one or more communications channels 1120 for instance one or more networks. While represented as a single element, there may be many homogenous and heterogeneous communication channels 1120 including for instance various types of networks. For example, many wireless or mobile communications devices 1108 are capable of wireless communications via various cellular networks, for instance various LTE, G4, G3 cellular voice and data networks. Also for example, many wireless or mobile communications devices 1108 are capable of wireless communications via various IEEE 802.11 compliant networks, for instance various WI-FI networks, or via BLUETOOTH or other wireless communications channels. The type of communications channel, whether networked or not, should not be considered limiting.

The operational environment 1100 may include various user computer systems 1122 (only one shown for sake of clarity of illustration) which allow specification of scent specifications or sets of scent delivery sequences. These user computer systems 1122 may be operated by various lay individuals, who define scent specifications or sets of scent delivery sequences for themselves or to share with others. These user computer systems 1122 may be operated by various professionals who are hired or whose primary occupation is to define scent specifications or sets of scent delivery sequences, for instance to be sold for use by others.

The operational environment 1100 may include various server computer systems 1124 (only one shown for sake of clarity of illustration) which allow storage and retrieval of scent specifications or sets of scent delivery sequences. These server computer systems 1124 may be operated by various individuals or entities, who provide services in providing sets of sequences, for instance selling sequences to others for their own use or to be given as gifts. Thus, the server computer system(s) 1124 may function as a Web portal for creating, editing, accessing, storing, purchasing, selling, sharing, renting, and/or gifting scent specifications or sets of scent delivery sequences, as well as other media content. The server computer system(s) 1124 may include one or more nontransitory computer- or processor-readable mediums which store one or more databases 1126.

The user and server computer systems 1122, 1124 will typically have the same or similar components or structures. The user and server computer systems 1122, 1124 may take any of a large variety of forms, many of which are commercially available. For instance, the user computer system(s) 1122 may take the form of personal or desktop computers, laptop computers, netbook computers, tablet computers, or even handheld processor-based devices such as personal digital assistants (PDAs) or smart phones. Also for instance, the server computer system(s) 1124 may take the form of personal or desktop computers, laptop computers, mini-computers, mainframe computers, or server cards or blades. Other computers or processor-based systems may be employed, and the specific type of computer system should not be considered limiting. What distinguishes these user and server computer systems 1122, 1124 from other user or server computer systems are the sets of instructions that the user or server computer systems execute to create or provide operational sequences (i.e., scent specifications or sets of scent delivery sequences) or the services these user or server computer systems respectively access or provide.

While most if not all of the components and structures will be readily recognized by those of skill in the computing arts, a basic description of a computer structure is provided for completeness of this description.

The user computer system 1122 and/or server computer system 1124 will at times be referred to in the singular herein, but this is not intended to limit the embodiments to a single device or system since in typical embodiments, there may be more than one user computer system 1122 and/or more than one server computer system 1124 involved. Unless described otherwise, the construction and operation of the various blocks shown in FIG. 11 are of conventional design. As a result, such blocks need not be described in further detail herein, as they will be understood by those skilled in the relevant art.

As shown in an enlarged portion, the user or server computer systems 1122, 1124 include one or more processors 1130 (e.g., microprocessors, graphics processors, digital signal processors), which may include one or more central processing units or cores and or integrated or discrete graphic processing units. The user or server computer systems 1122, 1124 may include one or more nontransitory media or memory structures. For example, the user or server computer systems will typically include some type of nonvolatile memory, such as read only memory (ROM) 1132, which typically stores instructions and data for initially configuring the microprocessor, for instance a basic input/output system (BIOS). The user or server computer systems 1122, 1124 will typically include some type of volatile memory, such as random access memory (RAM) 1134, which typically stores instructions and data during runtime for execution by the microprocessor in providing the desired operations or features. For example, the RAM 1134 may store an application for creating or defining scent specifications or sets of scent delivery sequences and/or for providing scent specifications or sets of scent delivery sequences to the systems 1102.

The user or server computer systems 1122, 1124 will typically include some type of long term volatile memory, such as one or more hard disk drives (HDD) 1136 and/or optical disk drive (ODD) 1138, which typically stores instructions and data for execution by the microprocessor 1130 in providing the desired operations or features. The HHD 1136 and/or ODD 1138 may include interfaces or controllers (not shown) coupled between such drives and one or more system buses 216, as is known by those skilled in the relevant art. In addition to reading, the ODD 1138 may be operable to burn instructions to optical disks for distribution. The HHD 1136 and/or ODD 1138, and their associated computer- or processor-readable storage media, may provide nonvolatile and non-transitory storage of computer- or processor-readable instructions, data structures, program engines and other data for the user and/or server computer systems 1122, 1124. Although illustrated employing a HDD 1136 and ODD 1138, those skilled in the relevant art will appreciate that other types of computer- or processor-readable storage media that can store instructions and/or data accessible by a computer may be employed, such as magnetic cassettes, flash memory, digital video disks ("DVD"), Bernoulli cartridges, RAMs, ROMs, smart cards, etc. Thus, any the nontransitory storage media may be employed including, for example spinning media such as HHDs 1136 or ODDs 1138 and/or stationary media such as solid-state drives or FLASH memory.

The HHD 1136 and/or ODD 1138 may store applications for creating or defining sets of scent specification or delivery sequences. The HHD 1136 and/or ODD 1138 may store sets of scent specification or delivery sequences created by a user of the user and/or server computer systems 1122, 1124.

The user and/or server computer systems 1122, 1124 will typically include some type of communications card and/or port. Such will typically take the form of a networking card or port 1140. Such may include any one or more conventional or to be developed wired, optical or wireless networking standards. Some examples include ETHERNET®, UNIVERSAL SERIAL BUS (USB®), FIREWIRE® 400, FIREWIRE® 800, THUNDERBOLT®, WI-FI®, BLUETOOTH®, various IEEE 802.11 protocols, CDMA, GSM®, LTE®, and other cellular network protocols. The type of communications should not be considered limiting.

One or more system buses 1142 communicatively couple various system components including the system memories to the processing units. The system bus(es) 1142 can employ any known bus structures or architectures, including memory bus(es) with memory controller, peripheral bus(es), local bus(es), instruction bus(es), data bus(es), address bus(es), and/or power bus(es).

The user and/or server computer systems 1122, 1124 can include one or more input devices such as a touch screen 1146 or keyboard 1148 and/or a pointing device such as a mouse 1150, and/or a graphical user interface that allow a user or operator to enter commands and information. Other input devices can include a microphone, joystick, game pad, tablet, scanner, etc. The user and/or server computer systems 1122, 1124 can include one or more monitors or display devices 1152, which may be communicatively coupled to the system bus 1142 via a video interface (not shown), such as a video adapter. The user and/or server computer systems 1122, 1124 can include other output devices, such as speakers, printers, etc.

Program engines can be stored in the system memory 1132, 1134, such as an operating system, one or more application programs, other programs or engines and program data. Application programs may include instructions that cause the processor(s) 1130 to automatically present a user interface for designing and/or editing or producing scent specifications or sets of scent delivery sequences, and optionally synchronizing the scent specifications or sets of scent delivery sequences with music, video, spoken word or other audio or visual content. Application programs may include instructions that cause the processor(s) 1130 to automatically store and/or deliver defined scent specifications or sets of scent delivery sequences. Application programs may include instructions that cause the processor(s) 1130 to store and/or deliver scent specifications or sets of scent delivery sequences based on various user identification information and/or device identification information.

Application programs may additionally or alternatively provide for revenue or compensation schema related to delivery of scent specifications or sets of scent delivery sequences. For example, application programs can electronically debit financial accounts in response to a user buying a scent specification or set of scent delivery sequence instructions. Also for example, the application programs may provide for delivery of scent specifications or sets of scent delivery sequences in exchange for watching and/or listening to various advertisements. Thus, the application programs may provide instructions that allow for sale, purchase, delivery, receipt, sharing and/or gifting of scent specifications or sets of scent delivery sequences with, or without advertisements.

Other program engines may include instructions for handling security such as password or other access protection and communications encryption. The system memory 1132, 1134 may also include communications programs, for example, a server program for permitting the server computer system 1124 to provide services and exchange data with other systems (e.g., systems 1102, user computer system 1122) or devices via the Internet, corporate intranets, extranets, or other networks (e.g., LANs, WANs) as described below, as well as other server applications executing on server computing systems. The server program may be markup language based, such as Hypertext Markup Language (HTML), Extensible Markup Language (XML) or Wireless Markup Language (WML), and operate with markup languages that use syntactically delimited characters added to the data of a document to represent the structure of the document. A number of server programs are commercially available such as those from Microsoft, Oracle, IBM and Apple.

While typically loaded or stored in the system memory 1132, 1134, the operating system, application programs, other programs/engines, program data and server programs can be stored on the HDD 1136 and or the ODD 1138, or any other nontransitory media.

The server computer system 1124 may serve as an exchange for scent specifications or sets of scent delivery sequences and related information, allowing creation, editing, storage, delivery, purchase, sharing, renting or leasing of scent specifications or sets of scent delivery sequences. Such may be with or without other media content, for instance music content (i.e., any audio content without regarding to format, including MP3 content) or video content (i.e., any audio visual content without regarding to format, including MP4 content), to which the scent specifications or sets of scent delivery sequences may be logically associated or even synchronized. As non-limiting examples, media content may include music, video, spoken word or other audio or visual content. Such allows display of available scent specifications or sets of scent delivery sequences. Such allows display of available media content. Such allows users, such as content consumers and/or content creators, to view available scent specifications, sets of scent delivery sequences and/or media content for downloading, sharing, editing, purchasing, or gifting. Such may also optionally cause insertion of advertisements in a flow or stream of content retrieved by content consumers.

Notably, there may be one or more Web-based server portals 1124, which may or may not be geographically distributed. Additionally, or alternatively, user interfaces for creation and/or editing of may be provided by the server computer system 1124 as a Web service or Software As Services option.

Scent sequences may be specified in a variety of ways, employing a variety of protocols. It is preferably if a standard protocol is adopted or developed, allowing scent sequences to be shared between users.

A scent sequence or scent event may have the following parameters: scent type, start time, end time, and potentially intensity. Start time and end time may specify the period during which a scent release actuator is active, causing release of a respective scent. For many implementations, the start time and end time define the period during which a scent release actuator actively heats scent media. For many scent release actuators, for example resistance heaters, it will take some period after the end time for the scent release actuator, as well as the scent media to cool. Thus, the end time may need to be adjusted to accommodate such cool down time. Where piezoelectric actuators are employed, the end time may automatically trigger active cooling, significantly reducing any cool down time. Such results in a more definite and dependable time at which a given scent is no longer being released. The active cooling may continue for a fixed or defined time, or may be specified by one or more parameters in the scent sequence information.

The various scent sequence parameters fit naturally in the standard MIDI protocol, used by most standard media content players for playing, creating and transferring music. It is important to note that the MIDI protocol is utilized by non-musical applications, especially if such applications are required to be synchronized to music.

Using this standard protocol may allow users from a wide range of experience and skills to create scent sequence information or "scent tracks" on a platform of the user's choice, whether it is a professional scent-composer creating scent tracks using common music production software, or an amateur matching scents to a favorite song using the various systems 100, 900, 1102, as described below.

Avoidance of a one to one (1:1) mapping between music and specific scents may be advantageous, particularly since there are an infinite number of ways to visualize music. Generating a scent track to accompany music requires a mapping that "feels right".

One simple way to achieve such is by synchronizing scent events to structural transitions (e.g., end of verse and beginning of chorus) and dynamic peaks. Under this generic mapping approach, scents will be released for a short period of time, in synchronization with these distinctive, discrete musical moments, with the intention of creating a sense of strong correlation between the music and the scent.

There are ways to ensure a scent track is consistent, regardless of the specific scent media present on a particular scent media carrier (e.g., cartridge). A configuration of four different scents on a single scent media carrier (e.g., cartridge) is used as an example, but is expandable to larger or small numbers of scent media.

For example, there might be very different scents for different types of cartridges. A standard arrangement of scents on scent media carriers may be specified. For instance, a convention may specify the following arrangement or mapping of scents for all scent media carriers (e.g., cartridges):

| | |
|---|---|
| A | Awakening |
| B | Stability |
| C | Tension |
| D | Resolution |

Using this generic mapping of scent location on the scent media carrier to mood, allows specification of scent types based on musical transitions. Thus, a scent sequence, for instance in form of a MIDI file or some other format, can be defined which, regardless of which scent media carrier (e.g., cartridge) is inserted to the drive unit of the system, causes a transition into a verse to trigger scent B, a beginning of a chorus to trigger scent A, a C-part to trigger scent C and a last chorus to trigger scent D. It is in the hands of the designer, supplier or entity that selects the scent media carrier (e.g., cartridge) to decide what specific scents (i.e., scent media) to employ, place or locate on the scent media carrier (e.g., cartridge).

Structural musical transitions can be relatively easily calculated by the application, calculated or cached at a server to be downloaded upon request, or retrieved from third party services for music analysis such as Echonest.

This generic mapping approach may help assure consistency of the scent sequence information or scent track across different scent media carrier, much like playing the same tune on different instruments.

The application can feature a dedicated user interface (UI) for the composition of the scent track. The UI can be a very simplistic sequencer that allows the user to associate scents to specific instants in a song. The user might be provided with pre-calculated points of interest, such as structural transition or dynamic peaks in the song. The user can then take these into consideration, but not necessarily conform to them, when the scent track is composed.

Thus, MIDI or some other format may be used as a scent transcription protocol. Automatic scent track generation associates short scent bursts to structural changes and dynamic peaks in the audio track. The application includes a simple interface for scent track composition.

Various nontransitory media discussed above may store information such as defined scent specifications or sequences or "scent tracks" in one or more data structures. Data structures may take a variety of forms, for example records associated with relational databases, a database itself, lookup tables, etc. The data structures may store a variety of different information or data.

A data structure may store defined scent specifications or sets of scent delivery sequences information or "scent tracks" in the form of a record with a variety of fields. Fields may specify a scent by a unique identifier, a generic identifier (e.g., scent type or group) or a position on a scent media carrier. Fields may specify a duration of scent release. Fields may specify a temperature for scent release or scent cooling.

Scent sequence information, specifications or "scent tracks" may, for example, be encoded as 8 bit sequences of instructions. For instance, the four most significant bits may specify a component, while the four least most significant bits may specify an action, state or the respective component. An example mapping of commands is illustrated in Tables A and B.

TABLE A

Component Identification

| Bit 7 | Bit 6 | Bit 5 | Bit 4 | Component |
|---|---|---|---|---|
| 0 | 0 | 0 | 1 | Complete Device |
| 0 | 0 | 1 | 0 | Phone |
| 0 | 0 | 1 | 1 | LED |
| 0 | 1 | 0 | 0 | Fan 1 |
| 0 | 1 | 0 | 1 | Fan 2 |
| 0 | 1 | 1 | 0 | Fan 3 |
| 0 | 1 | 1 | 1 | Peltier 1 |
| 1 | 0 | 0 | 0 | Peltier 2 |
| 1 | 0 | 0 | 1 | Peltier 3 |
| 1 | 0 | 1 | 0 | Peltier 4 |

TABLE B

State Identification

| Bit 3 | Bit 2 | Bit 1 | Bit 0 | State |
|---|---|---|---|---|
| 0 | 0 | 0 | 1 | ON |
| 0 | 0 | 1 | 0 | OFF |
| 0 | 0 | 1 | 1 | HOT |
| 0 | 1 | 0 | 0 | COLD |
| 0 | 1 | 1 | 1 | Status |

The above examples of data structures, and examples of specific types of information are intended to be illustrative and not limiting. In some instances, additional information may be employed and some of the illustrated information omitted. Also, different data structures may be employed and/or the information may be stored in different data structures or different ways. For example, a separate content provider specific data structure may be employed to store information related to respective content providers. Also for example, a separate advertiser data structure may be employed to store information related to respective advertisers.

Upon receipt of a scent sequence or scent track, a notification or an alert may be provided to the user. The notification may be a visual and/or aural and/or tactile. For example, a light (e.g., LED) may illuminate or flash, or a message (e.g., alphanumeric) may be displayed on a screen. A sound may be emitted by a speaker. A vibratory stimulation may be provide via one or more vibrators. The notification may be provided directly by the system 100, 900, 1002. Additionally or alternatively, the notification may be provided by a mobile communications device (e.g., smart phone) or media content player (e.g., MP3 player, IPOD®, tablet computer, netbook computer, laptop computer) 116 associated with the system 100, 900, 1002 or associated with the end user, whether or not presently communicatively coupled to the system 100, 900, 1002.

As described in more detail below, the present disclosure provides an apparatus which may be used in methods for inducing or enhancing emotional states (e.g., happiness, fear, disgust, pleasure, anger, cheerfulness, alertness, aggression, or melancholy) or inducing or enhancing physiological states (e.g., sleep, wakefulness, hunger, satiated, alertness, relaxation, or arousal) by selectively providing an olfactory stimulus in an emotional induction program or physiological induction program, respectively. In certain embodiments, the olfactory stimulus is provided in combination with visual (e.g., color, image, video) and/or auditory (e.g., tone, music, song) stimuli. The olfactory stimuli, optionally in combination with the visual or auditory stimuli, in the emotional or physiological induction program are selected for their capability of inducing or enhancing a desired emotion or physiological state in the user.

The olfactory stimuli are delivered through the apparatus provided in the present disclosure. Visual and auditory stimuli may be delivered using any mobile communications device, personal computer, electronic tablet, portable music player, portable viewing device, or the like. A control unit, which may comprise a computer or other programmable data processing apparatus, may be connected with the systems 100, 900, 1002 and other devices (e.g., visual stimulating device, auditory stimulating device, or sensor unit).

When an emotional or physiological induction program is initiated by a program, a user, or a remote individual, the systems 100, 900, 1002 emit a selected odor to the user. The emotional or physiological induction program may also transmit a selected image or sound to the user, concurrently with the odor or sequentially. The duration, intensity, and sequence of the olfactory, visual, or auditory stimuli may vary. The specific odor, image, or sound presented to the user in the emotional or physiological induction program is selected for its ability to induce or enhance the emotion or physiological state, or their association with the particular emotion or physiological state in the user. By way of example, if the emotional or physiological induction program selected is wakefulness, the systems 100, 900, 1002 may emit an odor of coffee to the user, optionally in combination with an image of a coffee-type beverage or a sound of a coffee maker. After experiencing the stimuli, the user experiences a feeling of wakefulness, without necessarily consuming a cup of coffee. In another example, if the emotional or physiological induction program selected is alarm, the systems 100, 900, 1002 may emit the odor of smoke to the user, optionally in combination with an image of a burning house or the sound of a crackling fire. In yet another example, if the emotional or physiological induction program selected is sleep, the systems 100, 900, 1002 may emit a relaxing odor such as lavender, optionally in combination with a soft or dimly lit image or white noise.

The duration, intensity, and sequence of the olfactory, visual, or auditory stimuli in a selected emotional or physiological induction program may be pre-set. It is also possible for the user to determine whether he/she has reached the desired emotional or physiological state and increase or decrease the intensity or duration of the emotional or physiological induction program through a control unit. Alternatively, a sensor unit that is connected to a control unit may detect biosignals from the user's body (e.g., heartbeat, body temperature, blood pressure, respiration rate, perspiration), and increase or decrease the intensity or duration of the emotional or physiological induction program if the biosignals conform to or fail to meet pre-set parameters for the selected emotional or physiological induction program. Additionally, a remote individual may desire to increase or decrease the intensity or duration of the emotional or physiological induction program of the user by sending signals to the control unit.

More specifically, olfactory stimuli are known to have effects on a recipient's physiological, emotional, or mental state. A variety of fields, including for example, human and veterinary medicine, psychology, psychiatry, advertising, retail, cosmetics, have investigated emotional, mental, and physiological responses to odors. Aromatherapy, which has long been in practice, is the use of fragrances to enhance, improve, or alter a person's mind, mood, cognitive function, or physical well-being. Aromachology is the study of the interrelationship between psychology and fragrance technology to elicit a variety of specific feelings and emotions via stimulation of olfactory pathways in the brain, particularly the limbic system.

Olfactory stimuli delivered by the systems provided herein, in conjunction with audio and/or visual stimuli, may be used to improve or alter the physiological response or state of the user. By way of example, the present invention may be used in the same manner as aromatherapy is being used as a primary or complementary therapy for acute and chronic pain. Aromatherapy is thought to enhance the parasympathetic response, facilitating deep relaxation, which alters pain perception (Buckle, 1999, Altern. Ther. Health Med. 5:42-51). Lavendar aromatherapy is currently in clinical trial in the U.S. for reduction of pain and anxiety during cervical colposcopy (Clinical Trial Identifier NCT01214304). Aromatherapy (e.g., clary sage, peppermint, lavender, and frankincense) is also in clinical trial in the U.S. for reduction of pain and anxiety during childbirth (Clinical Trial Identifier NCT01051726, see also, Burns et al., 2007, BJOG 114:838-844). Aromatherapy can also alleviate pain and anxiety in hospice patients (Louis and Kowalski, 2002, Am. J. Hosp. Palliat. Care 19:381-386). Postanesthesia lavender aromatherapy has been shown to reduce the demand for opioids in the immediate post-operative period in morbidly obese patients (Kim et al., 2007, Obesity Surgery 17:920-925). Sweet orange essential oil has been found to promote induction of anesthesia in children (Mehta et al., 1998, Anaesthesia 53:720-721). In another example, lavender, clary sage, and rose aromatherapy have been shown to improve menstrual cramps and the symptoms of dymenorrhea (Han et al., 2006, J. Alternative and Complementary Med. 12: 535-541). In yet another example, tea tree oil and citrus fragrance have been shown to have immunomodulatory properties (Golab et al., 2005, J. Appl. Biomed. 3:101-108; Komori et al., 1995, Neuroimmunomodulation 2:174-180). In another example, aromatherapy has been found to have sedative effects and to promote deep sleep (Goel et al., 2005, Chronobiology Intl. 22:889-904). The pleasantness of an odor was found to influence heart rate and arousal (measured by skin conductance) (Bensafi et al., 2002, Chem. Senses 27:703-709). In fact, aromatherapy has also been shown to affect the user on a molecular level. Seo et al. studied the effect of coffee bean aroma on the transciptome and proteome of rats stressed by sleep deprivation (2008, J. Agric. Food Chem. 56:4665-4673). Proteins that were up-regulated by the coffee bean aroma belonged to functional categories such as antioxidants, cell rescue, and energy metabolism.

Olfactory stimuli delivered by the systems provided herein, in conjunction with audio and/or visual stimuli, may also be used to improve or alter the emotional or psychological state of the user. For example, aromatherapy has been found to improve agitation and behavioral disturbances in patients with dementia (Ballard et al., 2002, J. Clin. Psychiatry 63:553-8; Lin et al., 2007, Int. J. Geriatric Psychiatry 22:405-410; Smallwood et al., 2001, Intl. J. Geriatric Psychiatry 16:1010-1013). Aromatherapy with massage has been shown to significantly improve depression and anxiety as compared to massage without essential oils (Lemon, 2004, Int. J. Aromatherapy 14:63-69). Komori et al., demonstrated that treatment with citrus fragrance could markedly reduce the doses of antidepressants necessary for treatment of depression (Neuroimmunomodulation 1995 2:174-180).

Olfactory stimuli delivered by the systems provided herein, in conjunction with audio and/or visual stimuli, may be used to improve cognitive function of the user. By way of example, aromatherapy with lavender was found to positively affect mood, EEG patterns of alertness, and ability to quickly and accurately perform math computations (Diego et al., 1998, Int. J. Neurosci. 96:217-224; Liu et al., 2004, Int. J. Aromatherapy 14:169-174). In another example, peppermint was found to increase alertness and enhance memory, while ylang-ylang impaired memory and lengthened processing speed, but increased calmness (Moss et al., 2008, Intl. J. Neurosci. 118:59-77).

Olfactory stimuli delivered by the systems provided herein, in conjunction with audio and/or visual stimuli, may be also be used for behavior modification of the user. For example, black pepper extract vapors have been found to reduce smoking withdrawal symptoms, including cigarette cravings and anxiety (Rose and Behm, 1994, Drug Alcohol Depend. 34:225-229). In another example, U.S. Patent Publication 2006/0222720 describes the use of *Vernonia cinerea* vapor as an appetite suppressant. Olfactory stimulation with grapefruit oil has been shown to reduce appetite and body weight in rats (Shen et al., 2005, Neurosci. Lett. 380:289-294). The scent of dark chocolate has also been found to have appetite suppression effects which correlated with decrease in ghrelin levels (Massolt et al., 2010, Regul. Pept. 161:81-86).

Further, the emotional, psychological, cognitive, and physiological effects of many odors are known in the art. For example, lemon, lemongrass, peppermint, and basil have been found to be psychologically stimulating, while lavender, rose, bergamont, chamomile, and sandalwood are relaxing (Manley, 1993, Crit. Rev. Food Science Nutr. 33:57-62; Tonoike et al., 1996, Electroenceph. Clin. Neurophysiol. 47:143-150; Buckle, 2001, Diabetes Spectrum 14:124-126). However, experimental evidence suggests that odor-related behavior is influenced by the emotional context in which that odor was first encountered. Studies have shown that hedonic assessment (pleasantness) of odors is learned through specific experiences, and when a novel odor is paired with an emotional event, hedonic assessment of that odor varied in correspondence with the associated emotion (Herz, 2005, Chem. Senses 30:i250-i251). Furthermore, when that odor is re-introduced to a recipient, it can influence behavior in a mood consistent manner (Id.).

In reference to the use of the present invention in combination with visual stimuli, studies have also demonstrated that the perception and experience of odors is influenced by visual cues. Color has been shown to affect perceived odor intensity (Zellner and Kautz, 1990, J. Exp. PSychol. Hum Percept. Perform. 16:391-397). Color has also been shown to influence odor identification and liking ratings (Zellner et al., 1991, Am. J. Psychol. 104:547-561). Appropriate odor-color (cherry-red) combinations have greater identification accuracy and faster response latencies than inappropriate odor-color combinations (lemon-red), and correctly identified odors were more likeable than odors that were incorrectly identified. In fact, color may also create a perceptual olfactory illusion, as a tasteless red coloring added to white wine causes the wine to be described by wine tasters with olfactory terms used for red wines (Morrot et al., 2001, Brain Lang. 79:309-320).

Modifications

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other systems, not necessarily the exemplary systems generally described above.

For instance, network and even non-networked topologies other than those illustrated and/or described may be employed.

The foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs) or programmable gate arrays. However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

Various methods and/or algorithms have been described. Some or all of those methods and/or algorithms may omit some of the described acts or steps, include additional acts or steps, combine acts or steps, and/or may perform some acts or steps in a different order than described. Some of the method or algorithms may be implemented in software routines. Some of the software routines may be called from other software routines. Software routines may execute sequentially or concurrently, and may employ a multi-threaded approach.

The various embodiments described above can be combined to provide further embodiments. Aspects of the embodiments can be modified, if necessary, to employ systems, circuits and concepts of the various patents, applications and publications to provide yet further embodiments. All of the commonly assigned US patent application publications, US patent applications, foreign patents, foreign patent applications and non-patent publications referred to in this specification and/or listed in the Application Data Sheet, including but not limited to U.S. Provisional Application No. 61/792,716, filed Mar. 15, 2013 and U.S. Provisional Application No. 61/817,180, filed Apr. 29, 2013 are incorporated herein by reference, in their entirety.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A portable scent delivery system, comprising:
a housing having at least a scent generation chamber that at least in use holds scent media, a scent mixing chamber and a filter chamber, the filter chamber separate from the scent mixing chamber and sized and dimensioned to hold filter medium;
a scent actuator which includes at least one heater controllably operable to selectively heat the scent media to cause release of one or more scents from the scent media in the scent generation chamber;
a first fan positioned in the housing and selectively operable to cause scent to move outwardly of the housing;
a second fan positioned in the housing and selectively operable to draw scent inwardly back to the housing;
a first valve positioned in the housing and selectively operable to control passage of scent from the scent mixing chamber to a configurable fluidly communicative conduit path;
a second valve positioned in the housing and selectively operable to control passage of scent to the filter chamber from the configurable fluidly communicative conduit path;
a scent port that is operable to selectively release scents, if any, from the scent chamber via convection in response to at least one end user input; and
a control subsystem communicatively coupled to receive a set of scent activation information which is at least in part remotely generated from the portable scent delivery system and which set of scent activation information represents an intensity of the one or more scents to be emitted, and which represents a duration period for emission of the one or more scents specified by a start time and an end time for the one or more scents, the control subsystem further communicatively coupled to control the at least one heater of the scent actuator in response to the received set of scent activation information and a cool down time of the scent media which is an amount of time between stopping a heating of the scent media and stopping emission of the at least one scent from the scent media.

2. The portable scent delivery system of claim 1, further comprising:
a user actuatable control communicatively coupled to provide the at least one end user input to cause the scent port to selectively release scents via convection at a time outside of the duration period.

3. The portable scent delivery system of claim 2 wherein the user actuatable control is coupled to the housing.

4. The portable scent delivery system of claim 1 wherein the control subsystem is communicatively coupled to receive the scent activation information from a mobile communications device or media content player.

5. The portable scent delivery system of claim 1 wherein the control subsystem is communicatively coupled to receive the scent activation information from a mobile communications device or media content player, and causes release of the scents in a synchronization with audio and/or images presented by the mobile communications device or media content player.

6. The portable scent delivery system of claim 1 wherein the scent actuator is controllably operable to release one or more scents in precisely controlled amounts at precisely controlled times.

7. The portable scent delivery system of claim 1 wherein the scent port is operable to release one or more scents in precisely controlled amounts at precisely controlled times.

8. The portable scent delivery system of claim 1 wherein the set of scent activation information is an integral part of a remotely generated scent experience package.

9. The portable scent delivery system of claim 1 wherein the scent actuator includes
at least one Peltier device operable to actively heat and alternatively actively cool the consumable scent media of the scent media carrier while the scent media carrier is received by the receiver.

10. The system of claim 1 wherein the housing includes at least a first compartment, a second compartment, and a third compartment, a receiver located in the first compartment, the system further comprising:
at least one filter, the at least one filter located in the second compartment, separate from the receiver which is located in the first compartment; and
the control subsystem located in the third compartment.

11. The system of claim 1, further comprising:
at least a scent delivery conduit that provides fluid communication between the scent chamber and the scent port that in use releases scent to a user from the scent delivery conduit.

12. The system of claim 11, further comprising:
at least a scent return conduit that provides fluid communication between the scent port and the filter chamber.

13. The system of claim 12 wherein the scent delivery and the scent return conduits form a scent circulation loop, and further comprising:
a scent port valve in the scent circulation loop, the scent port valve selectively operable to control passage of scents via the scent port.

14. The system of claim 1, further comprising:
a pendant having a scent port.

15. The system of claim 14, further comprising:
a first cable that runs from the housing to the scent port, the first cable including at least a scent delivery conduit that provides fluid communication between the scent chamber and the scent port that in use releases scent to a user from the scent delivery conduit.

16. The system of claim 1, further comprising:
at least one of the scent media carriers, which carries at least two consumable scent media in the form of a wax substrate with a respective lipophillic scent.

17. A portable scent delivery system, comprising:
a housing having at least a scent generation chamber that at least in use holds scent media;
a scent actuator which includes at least one heater controllably operable to selectively heat the scent media to cause release of one or more scents from the scent media in the scent generation chamber;
a scent port that is operable to selectively release scents, if any, from the scent chamber via convection in response to at least one end user input;
a control subsystem communicatively coupled to receive a set of scent activation information which is at least in part remotely generated from the portable scent delivery system and which set of scent activation information represents an intensity of the one or more scents to be emitted, and which represents a duration period for emission of the one or more scents specified by a start time and an end time for the one or more scents, the control subsystem further communicatively coupled to control the at least one heater of the scent actuator in response to the received set of scent activation information and a cool down time of the scent media which is an amount of time between stopping a heating of the scent media and stopping emission of the at least one scent from the scent media,
at least a scent delivery conduit that provides fluid communication between the scent chamber and the scent port that in use releases scent to a user from the scent delivery conduit; and
at least a scent return conduit that provides fluid communication between the scent port and the filter chamber, wherein the scent delivery and the scent return conduits are each respective pieces of stretched neoprene tubing with an inner diameter of approximately 1.5 millimeters.

18. A portable scent delivery system comprising:
a housing having at least a scent generation chamber that at least in use holds scent media;
a scent actuator which includes at least one heater controllably operable to selectively heat the scent media to cause release of one or more scents from the scent media in the scent generation chamber;
a pendant having a scent port, the scent port operable to selectively release scents, if any, from the scent chamber via convection in response to at least one end user input; and
a control subsystem communicatively coupled to receive a set of scent activation information which is at least in part remotely generated from the portable scent delivery system and which set of scent activation information represents an intensity of the one or more scents to be emitted, and which represents a duration period for emission of the one or more scents specified by a start time and an end time for the one or more scents, the control subsystem further communicatively coupled to control the at least one heater of the scent actuator in response to the received set of scent activation information and a cool down time of the scent media which is an amount of time between stopping a heating of the scent media and stopping emission of the at least one scent from the scent media; and
a first cable that runs from the housing to the scent port, the first cable including at least a scent delivery conduit that provides fluid communication between the scent chamber and the scent port that in use releases scent to a user from the scent delivery conduit,
wherein the first cable further includes at least a scent return conduit that provides fluid communication between the scent port and the filter chamber.

19. The system of claim 18 wherein the pendant includes at least a first portion and a second portion, the second portion pivotally mounted to the first portion for rotation relative thereto.

20. The system of claim 19 wherein the control subsystem activates at least one fan in response to orientation of the second portion of the pendant relative to the first portion of the pendant.

21. The system of claim 18, further comprising:
a touch sensor that senses human touch of at least a portion of the pendant; and
the control subsystem is communicatively coupled to control operation at least partially responsive to human touch of the pendant.

22. The system of claim 18, further comprising:
a motion sensor that senses movement of at least a portion of the pendant; and
the control subsystem is communicatively coupled to control operation at least partially responsive to movement of the pendant.

* * * * *